United States Patent
Whirley et al.

(10) Patent No.: US 8,666,714 B2
(45) Date of Patent: *Mar. 4, 2014

(54) VIRTUAL PROTOTYPING AND TESTING FOR MEDICAL DEVICE DEVELOPMENT

(75) Inventors: Robert G. Whirley, Santa Rosa, CA (US); Michael V. Chobotov, Santa Rosa, CA (US)

(73) Assignee: Trivascular, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/523,765

(22) Filed: Jun. 14, 2012

(65) Prior Publication Data

US 2012/0316854 A1    Dec. 13, 2012

Related U.S. Application Data

(60) Division of application No. 12/904,994, filed on Oct. 14, 2010, now Pat. No. 8,224,632, which is a continuation of application No. 09/679,725, filed on Oct. 4, 2000, now Pat. No. 7,840,393.

(51) Int. Cl.
*G06G 7/48* (2006.01)
*A61F 2/06* (2013.01)

(52) U.S. Cl.
USPC .............................................. 703/7; 623/1.11

(58) Field of Classification Search
USPC ............................................. 623/1.11; 703/7
See application file for complete search history.

(56) References Cited

U.S. PATENT DOCUMENTS

| | | |
|---|---|---|
| 4,742,464 A | 5/1988 | Duret et al. |
| 5,041,141 A | 8/1991 | Ypma et al. |
| 5,150,304 A | 9/1992 | Berchem et al. |
| 5,233,992 A | 8/1993 | Holt et al. |
| 5,273,038 A | 12/1993 | Beavin |
| 5,365,996 A | 11/1994 | Crook |
| 5,506,785 A | 4/1996 | Blank et al. |
| 5,590,261 A | 12/1996 | Sciaroff et al. |
| 5,594,651 A | 1/1997 | St. Ville |
| 5,601,084 A | 2/1997 | Sheehan et al. |
| 5,612,885 A | 3/1997 | Love |
| 5,798,924 A | 8/1998 | Eufinger et al. |
| 5,880,976 A | 3/1999 | DiGioia, III et al. |
| 5,926,650 A | 7/1999 | Suzuki |
| 6,201,543 B1 | 3/2001 | O'Donnell et al. |

(Continued)

FOREIGN PATENT DOCUMENTS

| | | |
|---|---|---|
| EP | 574098 | 12/1993 |
| WO | WO 03/015666 | 2/2003 |

OTHER PUBLICATIONS

Fuat G. Uler, Osama A. Mohammed, "A 3-D Finite Element Mesh Generator for Complex Volumes" IEEE Transactions on Magnetcis, vol. 30, No. 5 Sep. 1994, pp. 3559-3542.*

(Continued)

*Primary Examiner* — Dwin M Craig
(74) *Attorney, Agent, or Firm* — Grant Anderson LLP

(57) ABSTRACT

A system and method of developing better-designed medical devices, particularly cardiovascular stents and endovascular grafts. The system comprises a geometry generator, a mesh generator, a stress/strain/deformation analyzer, and a visualization tool. Using analysis, preferably non-linear analysis, the stress/strain/deformation analyzer determines the predicted stresses, strains, and deformations on the candidate medical device. Such stresses, strains, and deformations may optionally be simulated visually using a visualization tool.

28 Claims, 44 Drawing Sheets

(56) References Cited

U.S. PATENT DOCUMENTS

| | | | |
|---|---|---|---|
| 6,293,966 B1 * | 9/2001 | Frantzen | 623/1.15 |
| 6,301,496 B1 | 10/2001 | Reisfeld | |
| 6,381,562 B2 | 4/2002 | Keane | |
| 6,463,351 B1 | 10/2002 | Clynch | |
| 6,684,754 B2 | 2/2004 | Comer | |
| 7,840,393 B1 * | 11/2010 | Whirley et al. | 703/7 |
| 8,224,632 B2 | 7/2012 | Whirley | |
| 2002/0068968 A1 | 6/2002 | Hupp | |
| 2002/0103505 A1 | 8/2002 | Thompson | |
| 2007/0203679 A1 | 8/2007 | Macura et al. | |
| 2011/0029297 A1 | 2/2011 | Whirley | |

OTHER PUBLICATIONS

Seung Lee, Nicole Piersol, Francis Loth, Paul Fischer, Gary Leaf, Barry Smith, Ramana Yedevalli, Atif Yardimici, Noam Alperin, Lewis Schwartz, Automated Mesh Generation of an Arterial Bifurcation Based upon in Vivo MR Images, Proceedings of the 22$^{nd}$ Annual EMBS International Conference, Jul. 23-28, 2000, Chicago IL. pages 719-722.*

Bossart and Hollerbach "Finite Element Analysis of Human Joints," IEEE Signal Process Society 1996 International Conference on Image Processing Lausanne, Switzerland Sep. 16-19, 1996 (Preprint submitted from Lawrence Livermore National Laboratory).

Bozic et al.. Three-dimensional finite element modeling of a cervical vertebra: An investigation of burst fracture mechanism, J. Spinal Disorders, 7(2):102-110 (Apr. 1994).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography", Computers in Cardiology,. 261-264 (Sep. 1999).

Chang et al., "Computer aided stress analysis of the femur with prosthetic hip stem utilizing computer tomography," Bioengineering Conference, Proceedings of the 1993 IEEE, Nineteenth Annual Northeast, pp. 60-61, Mar. 18-19, 1993.

Chong et al., "A prototype simulator for endovascular repair of abdominal aortic aneurysms," 1997, W.B. Saunders Compant Ltd., pp. 330-333.

Christon et al. "Visualization of High Resolution, Three-Dimensional, Nonlinear Finite Element Analyses," Proceedings. Visualization '92 (Car. No. 92Ch3201-1) (1992).

De Hart, J., "A three-dimensional analysis of a fibre-reinforced aortic valve prosthesis," 1998, Elsevier Science Ltd., pp., 629-638.

Dooley et al., "Orthopedic Implant Design, Analysis, and Manufacturing System", Bioengineering Alliance of South Carolina, Clemson University, Rhodes Research Center, Clemson S.C. 29634, pp. 60-64, Jun. 8-10, 1988.

Dovey and Spelce "GRIZ Finite Element Analysis Results Visualization for Unstructured Grids: User Manual," Methods Development Group, Mechanical Engineering, Lawrence Livermore National Laboratory (Oct. 1993).

Dumoulin C. et al., "Mechanical behavior modeling of balloon-expandable stents", Journal of Biomechanics, vol. 33, No. 11, pp. 1461-1470 (available online Sep. 8, 2000).

Furusawa et al., "3D-FEM stress analysis in a walking cycle of a tibia replaced by TKA," (1997).

Elger et al. "The Influence of Shape on the Stresses in Model Abdominal Aortic Aneurysms," Transactions of the ASME 326:326-32 (1996).

Haimovitch et al., "Robust growth is forecast for endovascular repair of AAAs", The BBI Newsletter, vol. 26, No. 5, pp. 113-144, (May 2003).

Holzapfel et al., Large strain analysis of soft biological membranes: Formulation and finite element analysis, Elsevier Science; Oct. 1995, p. 45-61.

Hoover et al. "Parallel Algorithms for Finite Element Analysis (DYNA3D/NIKE3D)," UCRLJC-127647 Abstract. Lawrence Livermore National Laboratory Technical Publication. (1997).

How et al. "Mechanical Properties of Arteries and Arterial Grafts," Chapter 1 of Cardiovascular Biomaterials Hasting, G.W. (ed.) London; New York: Springer-Verlag, 1992 pp. 1-35.

Kelley et al, "Failure of All-ceramic Fixed Partial Dentures in vitro and in vivo: Analysis and Modeling"; Jun. 1995; J Dent Res 74(6); pp. 1253-1258.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 (1998).

Lee et al., "Automated Mesh Generation of an Arterial Bifurcation Based upon In Vivo MR Images", Jul. 23-28, 2000, World Congress on Medical Physics and Bioengineering, pp. 1-4.

Leotta et al., "Cross-Sectional Area Changes in Peripheral Vein Grafts Monitored by Three-Dimensional Ultrasound Imaging", University of Washington, Seattle, WA 98195, 2000 IEEE Ultrasonics Symposium, May 2000 pp. 1-4.

Leotta et al., "Cross-Sectional Area Changes in Peripheral Vein Grafts Monitored by Three-Dimensional Ultrasound Imaging"; 2000 IEEE Ultrasonic Symposium: May 2000: pp. 1865-1868.

Maker et al.; "NIKE3D, A nonlinear, implicit, three-dimensional finite element code for solid and structural mechanics user's manual"; Apr. 14, 1995.

Mosora et al. "Modeling the arterial wall by finite elements," Archives Internationales de Phvsiolonie, de Biochimica et de Biophvsique 101;185-191 (1992).

Mower et al. "Stress Distributions in Vascular Aneurysms: Factors Affecting Risk of Aneurysm Rupture," J. Surgical Research 55: 151-161 (1993).

Muccini et al., "Selection of the Best Element Type in the Finite Analysis of Hip Prostheses", Journal of Medical Engineering of Technology, vol. 24, No. 4 (Jul./Aug. 2000) pp. 145-148.

Nicholas, "Critical issues in high cycle fatigue," 1999 International Journal of Fatigue, vol., 21, pp. S221-S231.

Papageorgiou, G.L. and N.B. Jones, "Physical Modeling of the Arterial Wall. Part 2: Simulation of the Non-Linear Elasticity of the Arterial Wall," J. Biomed. Enn. 9:216-21 (1987).

Perry et al., "Finite Elemental Analysis of Ni-Ti Alloy Stent Deployment," Proceedings of the Second International Conference on SMST, Asilomar Conference Center, Pacific Gorve, CA, USA (1997).

Haridas et al., "Predictive Analysis at the Forefront of Medical Product Development", Medical Device & Diagnostic Industry Magazine, MDLDI, Oct. 1999.

Raboin, "Computational Mechanics Moves Ahead" May 1998, Science d Technology Review, May 1998 pp. 1-13.

Raghavan et al. "Ex Vivo Biochemical Behavior of Abdominal Aortic Aneurysm: Assessment Using a New Mathematical Model," Journal of Biomedical Engineering 24:573-582 (1996).

Rebelo et al.; "Finite element analysis for the design of Nitinol medical devices"; Pacific Consultants; 1999.

Rogers et al., "Balloon-Artery Interactions During Stent Placement: A Finite Element Analysis Approach to Pressure, Compliance, and Stent Design as Contributors to Vascular Injury", 1999; American Heart Association: pp. 378-383.

Santosh et al., "Interface Mechanics in Lower-Limb External Prosthetics: A review of Finite Elemental Models", 1996 IEEE Transactions on Rehabilitation Engineering, vol. 4. No. 4, pp. 288-302.

Simon et al. "Finite Element Models for Arterial Wall Mechanics" J. Biomechanical Engineering 115:489-96 (1993).

Speck et al., "GRIZ Finite Element Analysis Results Visualization for Unstructured Grids"; Mar. 1996; Lawrence Livermore National Laboratory; contents, pp. 1-2, 21-27.

Stern et al., "Interactive Definition of Endoluminal Aortic Stent Size and Morphology Based on Virtual Angioscopic Rendering of 3D Magnetic Resonance Angiography (MRA)," Cars. Computer Assisted Radioloav and Suraely. Proceedings of the International Symposium on Computer Assisted Radiology and Surgery:176-180 (Jun. 1999).

(56) References Cited

OTHER PUBLICATIONS

Tanaka et al. "Inelastic Constitutive Modeling of Arterial and Ventricular Walls," Computational Biomechanics Hayashi, Ishikawa (eds.) Springer Press (1996) pp. 137-163.

Taylor et al. Finite Element Modeling of Three-Dimensional Pulsatile Flow in the Abdominal Aorta: Relevance to Atherosclerosis; Annals of Biomedical Engineering; vol. 26; 1998; pp. 975-987.

Testi et al.. Risk of fracture in elderly patients: A new predictive index based on bone mineral density and finite element analysis, Computer Methods and Programs in Biomedicine, 60:23-33 (Jul. 1999).

Uflacker et al., "Endovascular treatment of abdominal aortic aneurysms: a review", 11:739-753 (2001).

Vito et al. "Stress Analysis of the Diseased Arterial Cross-section," 1990 Advances in Bioengineering American Society of Mechanical Engineers, Bioengineering Division (Publication) BED v.17, ASME:New York, (1990). pp. 273-276.

Whitcher, "Simulation of in-vivo loading conditions of nitinol vascular stent structures,": 1997, Elsevier Science Ltd., pp. 1005-1011.

Witcher et al., "A Finite Element Treatment of the In-Vivo Loading Conditions of NITI Vascular Stent and Graft Structures," Proceedings of the Second International Conference on SMST, Asilomar Conference Center Pacific Grove, CA USA 1997.

Xu et at. "Coupled Modeling of Blood Flow and Arterial Interactions by The Finite Element Method," Proceedings of the Computers in Cardiology 1993 IEEE Computer Society Press Sep. 5-8, 1993 pp. 687-690.

Zacek et al., "Numerical stimulation of the blood flow in the human cardiovascular system", 1995 Elsevier Science Ltd., pp. 13-20.

Office Action dated: Apr. 4, 2012 in U.S. Appl. No. 12/904,994, filed Oct. 14, 2010, published as: US 2011-0029297 on Feb. 3, 2011 and issued as: 8,224,632 on Jul. 17, 2012.

Office Action Response dated: Feb. 21, 2012 in U.S. Appl. No. 12/904,994, filed Oct. 14, 2010, published as: US 2011-0029297 on Feb. 3, 2011 and issued as: 8,224,632 on Jul. 17, 2012.

Office Action dated: Sep. 22, 2011 in U.S. Appl. No. 12/904,994, filed Oct. 14, 2010, published as: US 2011-0029297 on Feb. 3, 2011 and issued as: 8,224,632 on Jul. 17, 2012.

Office Action Response dated: Jul. 29, 2011 in U.S. Appl. No. 12/904,994, filed Oct. 14, 2010, published as: US 2011-0029297 on Feb. 3, 2011 and issued as: 8,224,632 on Jul. 17, 2012.

Office Action dated: Jan. 31, 2011 in U.S. Appl. No. 12/904,994, filed Oct. 14, 2010, published as: US 2011-0029297 on Feb. 3, 2011 and issued as: 8,224,632 on Jul. 17, 2012.

Office Action dated: Jul. 15, 2010 in U.S. Appl. No. 09/679,725, filed Oct. 4, 2000 and Issued as: 7,840,393 on Nov. 23, 2010.

Office Response dated: Apr. 27, 2010 in U.S. Appl. No. 09/679,725, filed Oct. 4, 2000 and issued as: 7,840,393 on Nov. 23, 2010.

Office Action dated: Oct. 27, 2009 in U.S. Appl. No. 09/679,725, filed Oct. 4, 2000 and Issued as: 7,840,393 on Nov. 23, 2010.

Office Response dated: Oct. 15, 2009 in U.S. Appl. No. 09/679,725, filed Oct. 4, 2000 and Issued as: 7,840,393 on Nov. 23, 2010.

Office Action dated: Apr. 20, 2009 in U.S. Appl. No. 09/679,725, filed Oct. 4, 2000 and Issued as: 7,840,393 on Nov. 23, 2010.

Office Response dated: Mar. 10, 2009 in U.S. Appl. No. 09/679,725, filed Oct. 4, 2000 and Issued as: 7,840,393 on Nov. 23, 2010.

Office Response dated: Feb. 17, 2009 in U.S. Appl. No. 09/679,725, filed Oct. 4, 2000 and Issued as: 7,840,393 on Nov. 23, 2010.

Office Action dated: Sep. 18, 2008 in U.S. Appl. No. 09/679,725, filed Oct. 4, 2000 and Issued as: 7,840,393 on Nov. 23, 2010.

Office Response dated: Aug. 26, 2008 in U.S. Appl. No. 09/679,725, filed Oct. 4, 2000 and Issued as: 7,840,393 on Nov. 23, 2010.

Office Action dated: Dec. 6, 2007 in U.S. Appl. No. 09/679,725, filed Oct. 4, 2000 and Issued as: 7,840,393 on Nov. 23, 2010.

Office Response dated: Oct. 11, 2007 in U.S. Appl. No. 09/679,725, filed Oct. 4, 2000 and Issued as: 7,840,393 on Nov. 23, 2010.

Office Action dated: Jun. 11, 2007 in U.S. Appl. No. 09/679,725, filed Oct. 4, 2000 and Issued as: 7,840,393 on Nov. 23, 2010.

Office Response dated: Mar. 27, 2007 in U.S. Appl. No. 09/679,725, filed Oct. 4, 2000 and Issued as: 7,840,393 on Nov. 23, 2010.

Office Action dated: Dec. 22, 2006 in U.S. Appl. No. 09/679,725, filed Oct. 4, 2000 and Issued as: 7,840,393 on Nov. 23, 2010.

Office Response dated: Nov. 15, 2006 in U.S. Appl. No. 09/679,725, filed Oct. 4, 2000 and Issued as: 7,840,393 on Nov. 23, 2010.

Office Action dated: Jul. 11, 2006 in U.S. Appl. No. 09/679,725 filed: Oct. 4, 2000 and Issued as: 7,840,393 on Nov. 23, 2010.

Office Response dated: Apr. 24, 2006 in U.S. Appl. No. 09/679,725 filed: Oct. 4, 2000 and Issued as: 7,840,393 on Nov. 23, 2010.

Office Action dated: Feb. 7, 2006 in U.S. Appl. No. 09/679,725, filed Oct. 4, 2000 and Issued as: 7,840,393 on Nov. 23, 2010.

Office Response dated: Jun. 8, 2005 in U.S. Appl. No. 09/679,725, filed Oct. 4, 2000 and Issued as: 7,840,393 on Nov. 23, 2010.

Office Action dated: Aug. 24, 2004 in U.S. Appl. No. 09/679,725, filed Oct. 4, 2000 and Issued as: 7,840,393 on Nov. 23, 2010.

"Modeling the Biomechanics of Human Joints and Prosthetics Implants" Lawrence Livermore National Laboratory (http://www-iscr.llnl.gov) 1995.

* cited by examiner

FIG. 5A

```
Line  Command
1     c *** Slotted Tube Integrated Stent Design Simulation: istent.run ****
2     c
3     c ----------------- parameter settings -------------------
4     c
5     c .... inike=1 => make nike file; inike=0 => make dyna file
6     c .... imodel = 0 => full 3 segment model with interconnects
7     c            = 1 => 3-crown segment only
8     c            = 2 => 6-crown segment only
9     c            = 3 => 12-crown segment only
10    c .... isym = 0 => full 360 deg model
11    c           = 1 => symmetric model
12    c .... isim_mode:  type of simulation
13    c           = 1: => radial force to R_f = X% R_0, restoring stress mat'l
14    c           = 2: => flat plate force, restoring stress mat'l
15    c           = 3: => predelivery compression, loading stress mat'l
16    c           = 4: => initial expansion
17    c           = 5: => frequency analysis
18    c .... refine = X => add X elements via mseq in each direction
19    c                of the cross section
20    c
21    parameter inike 1 ;
22    parameter imodel 0 ;
23    parameter isym 0 ;
24    parameter isim_mode 4 ;
25    parameter refine 2 ;
26    c
27    para Tighten [0.9];     c helps 'tighten' or stiffen spline
28                            c range (0.5,1) (probably should not change)
29    c
30    c ----------------- parameter settings -------------------
31    c
32    c .... ========= design parameters =========================
33    c
34    c Note: Adjust specified OD for each segment considering the wall
35    c       thickness for that segment so that ID's match in a consistent
36    c       way for the tube blank from which they were cut.
37    c
38    c Upper segment --- 3 crowns
39    c Middle segment -- 6 crowns
```

FIG. 5B

| Line | Command |
|---|---|
| 40 | c Lower segment --- 12 crowns (conical) |
| 41 | c |
| 42 | c Parameters for 3-crown segment |
| 43 | c |
| 44 | para |
| 45 | RCyl3 [.5*2/25.4] |
| 46 | dCIA3 [-.00]   c delta of center of inner arc for 3 crown segment (-:0) |
| 47 | dCOA3 [0]     c delta of center of outer arc for 3 crown segment (0:+) |
| 48 | CW3 [.007]    c Circumferential width of segments for 3 crowns |
| 49 | RW3 [.005]    c Radial width for 3 crowns |
| 50 | NRA3 [.0095]  c normal radius of smaller cylinders (arcs) |
| 51 | c for 3 crowns |
| 52 | Ht3 [0.224]   c distance from center of upper arcs |
| 53 | c to center of lower arcs for 3 crowns |
| 54 | NLegEl3 [12]; c number of elements along the leg |
| 55 | |
| 56 | c |
| 57 | c Parameters for 6-crown segment |
| 58 | c |
| 59 | para |
| 60 | RCyl6 [.5*2/25.4] c outside radius for 6 crown segment |
| 61 | dCIA6 [0]     c delta of center of inner (smaller) arc for 6 crown segment(-:0) |
| 62 | dCOA6 [0.002] c delta of center of outer (larger) arc for 6 crown segment (0:+) |
| 63 | CW6 [.009]    c Circumferential width of segments for 6 crowns |
| 64 | RW6 [.009]    c Radial width for 6 crowns |
| 65 | NRA6 [.0105]  c normal radius of smaller cylinders (arcs) |
| 66 | c for 6 crowns |
| 67 | Ht6 [.115]    c distance from center of upper arcs |
| 68 | c to center of lower arcs for 6 crowns |
| 69 | NLegEl6 [12]; c number of elements along the leg |
| 70 | |
| 71 | c |
| 72 | c Parameters for 12-crown segment |
| 73 | c |
| 74 | para |
| 75 | dCIA12 [0]    c delta of center of inner arc for 12 crown segment (-:0) |

FIG. 5C

| Line | Command | |
|---|---|---|
| 76 | dCOA12 [0] | c delta of center of outer arc for 12 crown segment (0:+) |
| 77 | CW12 [.005] | c Circumferential width of segments for 12 crowns |
| 78 | RW12 [.008] | c Radial width for 12 crowns |
| 79 | NRA12 [.006] | c normal radius of smaller cylinders (arcs) |
| 80 | | c for 12 crowns |
| 81 | Ht12 [.050] | c distance from center of upper arcs |
| 82 | | c to center of lower arcs for 12 crowns |
| 83 | | c (measured along the leg, not necessarily in |
| 84 | | c the z direction) |
| 85 | c first outside radius for 12 crown segment (near other segments) | |
| 86 | RCyl12_1 [.5*2/25.4 - (.016-%RW12)] | |
| 87 | c second outside radius for 12 crown segment (bottom) | |
| 88 | RCYl12_2 [.5*1.4/25.4 - (.016-%RW12)] | |
| 89 | c | |
| 90 | NLegEl12 [10]; | c number of elements along the leg |
| 91 | | |
| 92 | c | |
| 93 | c Interconnects | |
| 94 | c | |
| 95 | | |
| 96 | c | |
| 97 | c Upper interconnects | |
| 98 | c | |
| 99 | para HIUp [.02] | c height of interconnect |
| 100 | FRUp [.005] | c fillet radius for blend |
| 101 | ICWUp [.006] | c circumferential width |
| 102 | IRWUp3 [.005] | c radial width at 3-crown end |
| 103 | IRWUp6 [.006]; | c radial width at 6-crown end |
| 104 | | |
| 105 | c | |
| 106 | c S-interconnects | |
| 107 | c | |
| 108 | para SIVer [.01] | c vertical distance between upper or lower arc centers |
| 109 | | c also the distance from the vertical mid-line to |
| 110 | | c the first arc center |
| 111 | SIHor [.010] | c horizontal distance between upper two or |
| 112 | | c lower two arc centers |
| 113 | SIr [.004] | c arc radius |

FIG. 5D

| Line | Command |
|---|---|
| 114 | SIrO [%SIr+%ICWUp/2]  c outer radius |
| 115 | SIrI [%SIr-%ICWUp/2]; c inner radius |
| 116 | |
| 117 | c |
| 118 | c Lower interconnects |
| 119 | c |
| 120 | para HILr   [.031]   c height of interconnect |
| 121 | FRLr    [.010]    c fillet radius for blend |
| 122 | ICWLr   [.007]   c circumferential width |
| 123 | IRWLr6  [.005]   c radial width at 6-crown end |
| 124 | IRWLr12 [.005];  c radial width at 12-crown end |
| 125 | |
| 126 | c |
| 127 | c .... ======== design parameters ======== |
| 128 | c |
| 129 | c .... set cylinder ID & OD for compression |
| 130 | c |
| 131 | if (%isim_mode.le.3) then |
| 132 | parameter ricompcyl [1.1*max(%RCyl3,%RCyl6,%RCyl12_1,%RCyl12_2)] ; |
| 133 | parameter rocompcyl [1.4*max(%RCyl3,%RCyl6,%RCyl12_1,%RCyl12_2)] ; |
| 134 | c |
| 135 | c .... set cylinder ID & OD for expansion |
| 136 | c |
| 137 | elseif (%isim_mode.eq.4) then |
| 138 | parameter rocompcyl [0.95*(min(%RCyl3,%RCyl6,%RCyl12_1,%RCyl12_2)-%RW6)] ; |
| 139 | parameter ricompcyl [0.7*(min(%RCyl3,%RCyl6,%RCyl12_1,%RCyl12_2)-%RW6)] ; |
| 140 | endif |
| 141 | c |
| 142 | c |
| 143 | c Materials assignments |
| 144 | c |
| 145 | parameter matst12 3 ; |
| 146 | parameter matst6  4 ; |
| 147 | parameter matst3  5 ; |

FIG. 5E

| Line | Command |
|------|---------|
| 148 | parameter mati126 6 ; |
| 149 | parameter mati63 7 ; |
| 150 | c |
| 151 | c |
| 152 | if (%isim_mode.eq.1) then |
| 153 |    echo *** Radial Force Simulation *** |
| 154 | elseif (%isim_mode.eq.2) then |
| 155 |    echo *** Flat Plate Force Simulation *** |
| 156 | elseif (%isim_mode.eq.3) then |
| 157 |    echo *** Predelivery Compression Simulation *** |
| 158 | elseif (%isim_mode.eq.4) then |
| 159 |    echo *** Initial Expansion Simulation *** |
| 160 | elseif (%isim_mode.eq.5) then |
| 161 |    echo *** Natural Frequency Analysis *** |
| 162 | else |
| 163 |    echo !!! ERROR: illegal isim_mode !!! |
| 164 |    interrupt |
| 165 | endif |
| 166 | c |
| 167 | c -------------------- analysis options -------------------- |
| 168 | title stent initial expansion simulation |
| 169 | c |
| 170 | c   *** DYNA3D Analysis Options *** |
| 171 | c |
| 172 | if (%inike.eq.0) then |
| 173 |   echo Making DYNA3D input file |
| 174 |   dyna3d |
| 175 |     dynaopts |
| 176 |     term 5.0e-5 |
| 177 |     plti 1.e-6 |
| 178 |     prti 5.0e-6 |
| 179 |   c |
| 180 |   c .... DR options |
| 181 |   c |
| 182 |     itrx 500 |
| 183 |     tolrx 1.0e-2 |
| 184 |     drdb |
| 185 |   c |
| 186 |   c .... thermal effects option - temp from load curve 1 |

FIG. 5F

| Line | Command |
|------|---------|
| 187 | c |
| 188 | teo 1 |
| 189 | c |
| 190 | tssf 0.0 |
| 191 | c |
| 192 | c print initial time step size |
| 193 | c |
| 194 | c prtflg 1 |
| 195 | c |
| 196 | c .... turn off (0) or on (1) SAND database flag |
| 197 | c |
| 198 | edsdf 0 |
| 199 | c |
| 200 | nrest 90000 |
| 201 | nrunr 95000 ; |
| 202 | c |
| 203 | c .... DYNA3D discrete nodes impacting surface - stent to cyl |
| 204 | c             * one side (180 deg) * |
| 205 | c |
| 206 | sid 1 dni |
| 207 | c sfif |
| 208 | c mfif |
| 209 | pnlts 1.0e-0 |
| 210 | pnltm 1.0e-0 |
| 211 | ; |
| 212 | c |
| 213 | c .... DYNA3D discrete nodes impacting surface - stent to cyl |
| 214 | c             * opposite side * |
| 215 | c |
| 216 | c sid 2 dni |
| 217 | c sfif |
| 218 | c mfif |
| 219 | c pnlts 1.0e-4 |
| 220 | c pnltm 1.0e-4 |
| 221 | c ; |
| 222 | c |
| 223 | c .... end DYNA3D commands |
| 224 | c |
| 225 | endif |

FIG. 5G

```
Line  Command
226   c
227   c
228   c    *** NIKE3D Analysis Options ***
229   c
230   if (%inike.eq.1) then
231     echo Making NIKE3D input file . . .
232     nike3d
233     nikeopts
234       nstep 5
235       delt 0.2
236       anal stat
237   c
238   c .... step tol of 1e-8 seems OK for predel compression
239   c
240   if (%isim_mode.eq.1.or.%isim_mode.eq.2) then
241       dctol -1.0e-8
242   elseif (%isim_mode.eq.3) then
243       dctol -1.0e-6
244   endif
245   c
246   c .... max iterations per stiffness reform
247   c
248       nibsr 20
249   c
250   c .... max stiffness reforms per step
251   c
252       msrf 20 ;
253   c
254   c .... temperatures follow load curve 1
255   c    ** manually add tref=1.0 on matl 2 control card cols 26-35 **
256   c
257       teo 1
258   if (%isim_mode.eq.1.or.%isim_mode.eq.2) then
259       iprt 1
260   elseif (%isim_mode.eq.3.or.%isim_mode.eq.4) then
261       iprt 25
262   endif
263     iplt 1
264     nsbrr 1
```

FIG. 5H

| Line | Command |
|---|---|
| 265 | stifcore 1 |
| 266 | bfgscore |
| 267 | bwmo new |
| 268 | echo Bandwidth minimization ACTIVATED with "NEW" option |
| 269 | c |
| 270 | c element constitutive data incore |
| 271 | c |
| 272 | bfor 10 |
| 273 | sfor 10 |
| 274 | bef 11 |
| 275 | c |
| 276 | c .... linear solver |
| 277 | c |
| 278 | lsolver fissle |
| 279 | c |
| 280 | c .... solid element stent contact surface |
| 281 | c |
| 282 | sid 1 sv |
| 283 | c |
| 284 | if (%isim_mode.eq.1) then |
| 285 | c |
| 286 | c |
| 287 | pnlt 1.0e-5 |
| 288 | elseif (%isim_mode.eq.2) then |
| 289 | pnlt 0.00001 |
| 290 | elseif (%isim_mode.eq.3) then |
| 291 | c |
| 292 | c .... essential to adjust penalty |
| 293 | c |
| 294 | pnlt 1.0e+4 |
| 295 | elseif (%isim_mode.eq.4) then |
| 296 | pnlt 1.0e-5 |
| 297 | c iaug 1 ; |
| 298 | endif |
| 299 | ; |
| 300 | c |
| 301 | c .... slidesurface between interconnects and segments |
| 302 | c |
| 303 | sid 2 tied |

| Line | Command |
|------|---------|
| 304 | ; |
| 305 | c |
| 306 | c .... NIKE3D shell geometric stiffness (HL only) |
| 307 | c |
| 308 |   segs 1 ; |
| 309 | c |
| 310 | c .... end NIKE3D section |
| 311 | c |
| 312 | endif |
| 313 | c |
| 314 | c .... symmetry planes |
| 315 | c |
| 316 | if(%isym.eq.1) then |
| 317 | c |
| 318 | c .... Symmetric Model |
| 319 | c   theta=-60 and +60 symmetry to remove rigid body modes |
| 320 | c |
| 321 | c plane 1 |
| 322 | c  0.0 0.0 0.0 |
| 323 | c  [-sin(60)] [-cos(60)] 0.0 |
| 324 | c   0.0005 symm ; |
| 325 | c plane 2 |
| 326 | c  0.0 0.0 0.0 |
| 327 | c  [-sin(60)] [cos(60)] 0.0 |
| 328 | c   0.0005 symm ; |
| 329 | c |
| 330 | else |
| 331 | c |
| 332 | c .... symmetry planes to remove rigid body modes for full model |
| 333 | c |
| 334 | plane 1 |
| 335 |   0.0 0.0 0.0 |
| 336 |   1.0 0.0 0.0 |
| 337 |    .0005 symm ; |
| 338 | plane 2 |
| 339 |   0.0 0.0 0.0 |
| 340 |   0.0 1.0 0.0 |
| 341 |    .0005 symm ; |
| 342 | c plane 3 |

FIG. 5I

| Line | Command |
|------|---------|
| 343 | c   0.0  0.0  0.0 |
| 344 | c   0.0  0.0  TBD |
| 345 | c    .0005 symm ; |
| 346 | endif |
| 347 | c |
| 348 | c |
| 349 | if (%inike.eq.0) then |
| 350 | c |
| 351 | c .... Load Curves for DYNA3D  **ADD DR FLAG TO INPUT FILE ** |
| 352 | c |
| 353 | if (%isim_mode.eq.1) then |
| 354 | c |
| 355 | c .... radial force |
| 356 | c |
| 357 | lcd 1 |
| 358 |     0.000E+00 1.000E+00 |
| 359 |     7.500E-03 2.250E+04 |
| 360 |     1.000E-00 2.250E+04 ; |
| 361 | c   1.000E-02 3.000E+04 |
| 362 | c   1.000E-00 3.000E+04 ; |
| 363 | elseif (%isim_mode.eq.2) then |
| 364 | c |
| 365 | c .... flat plate compression, lcd 1 not used (dummy definition) |
| 366 | c |
| 367 | quit |
| 368 | c |
| 369 | elseif (%isim_mode.eq.3) then |
| 370 | c |
| 371 | c .... predelivery compression strain |
| 372 | c |
| 373 | lcd 1 |
| 374 |     0.000E+00 1.000E+00 |
| 375 |     1.000E-02 2.008E+05 |
| 376 |     1.000E-00 2.008E+05 ; |
| 377 | endif |
| 378 | c |
| 379 | c .... load curve #2 only used for flat plate compression |
| 380 | c |
| 381 | lcd 2 |

FIG. 5J

```
Line  Command
382      0.000E+00  0.000E+00
383      1.000E+00  0.000e-00 ;
384   endif
385   c
386   if (%inike.eq.1) then
387   c
388   c .... ******** Load Curves for NIKE3D **********
389   c
390   if (%isim_mode.eq.1) then
391   c
392   c .... radial force
393   c
394   lcd 1
395      0.000E+00  1.000E+00
396      1.000E+00  2.000E+03 ;
397   elseif (%isim_mode.eq.2) then
398   c
399   c .... flat plate compression
400   c
401   lcd 1
402      0.000E+00  1.000E+00
403      1.000E+00  0.000E+00 ;
404   elseif (%isim_mode.eq.3) then
405   c
406   c .... predelivery compression strain
407   c
408   lcd 1
409      0.000E+00  1.000E+00
410      1.000E+00  2.008E+03 ;
411   elseif (%isim_mode.eq.4) then
412   c
413   c .... initial expansion strain
414   c
415   lcd 1
416   c .... thermal load (activate TEO above)
417   c   0.000E+00   1.000E+00
418   c   1.000E+00  -2.008E+04 ;
419   c .... prescribed displacement
420      0.000E+00  0.000E+00
```

```
Line  Command
421       1.000E+00  1.000E-02 ;
422   endif
423   c
424   c ------------------- stent parts ----------------
425   c
426   include irss.tg
427   c
428   c ------------------- stent materials ----------------
429   c
430   if (%inike.eq.1) then
431       if (%isim_mode.eq.1.or.%isim_mode.eq.2) then
432           include istent.mats_nike_solid
433           echo   model for radial force/flat plate analysis
434       elseif (%isim_mode.eq.3) then
435           include istent.mats_compress_nike_solid
436           echo   model for predelivery compression strain
437       elseif (%isim_mode.eq.4) then
438           include istent.mats_compress_nike_solid
439           echo   model for initial expansion strain
440       endif
441   c
442   elseif (%inike.eq.0) then
443       if (%isim_mode.eq.1.or.%isim_mode.eq.2) then
444           include istent.mats_dyna_solid
445           echo   model for radial force/flat plate analysis
446       elseif (%isim_mode.eq.3) then
447           include istent.mats_compress_dyna_solid
448           echo   model for predelivery compression strain
449       elseif (%isim_mode.eq.4) then
450           include istent.mats_compress_dyna_solid
451           echo   model for initial expansion strain
452       endif
453   endif
454   c
455   c .... cylindrical compression for radial force or predelivery compression
456   c
457   if (%isim_mode.eq.1.or.%isim_mode.eq.3.or.%isim_mode.eq.4) then
458   c
459      if (%isym.eq.1) then
```

| Line | Command |
|---|---|
| 460 | include cylinder.parts_sym |
| 461 | else |
| 462 | include cylinder.parts |
| 463 | endif |
| 464 | c |
| 465 | if (%inike.eq.1) then |
| 466 | include cylinder.materials_nike |
| 467 | elseif (%inike.eq.0) then |
| 468 | include cylinder.materials_dyna |
| 469 | endif |
| 470 | endif |
| 471 | c |
| 472 | stp .01 |
| 473 | merge |
| 474 | c |

FIG. 5M

```
1    c ********** TPEG Inflatable Proximal Seal Simulation ******************
2    c              (seal.run)
3    c              March, 1999
4    c
5    c ---------------- parameter settings ------------------
6    c
7    c .... analytical model aorta geometric parameters
8    c       (distortion is 4-lobe)
9    c
10   parameter r_aorta [10.0/25.4] ;
11   parameter thk_aorta [1.0/25.4] ;
12   parameter amp_plaque [0.0/25.4] ;
13   c
14   parameter ro_aorta [%r_aorta+%thk_aorta] ;
15   c
16   c ....  -- TPEG Design Parameters --
17   c
18   parameter r_tpeg [10/25.4] ;
19   parameter r_ps [3/25.4] ;
20   parameter l_tpeg 2.0 ;
21   parameter l_flap 0.25 ;
22   c
23   parameter graft_wall_thick [6*0.0013] ;
24   parameter cuff_wall_thick [3*0.0013] ;
25   parameter flap_wall_thick [6*0.0013] ;
26   c
27   c
28   c .... Pressures and load curve assignments
29   c
30   parameter P_hemo 2.32 ;
31   parameter P_cuff 3.0 ;
32   c
33   parameter lc_hemo 1 ;
34   parameter lc_proxcuff 3 ;
35   c
36   c .... TPEG folding simulation parameters
37   c
38   parameter vel_fold 20.0 ;
39   parameter t_fold [0.25/%vel_fold] ;
40   parameter t_init 0.0e-3 ;
41   c
42   c
```

FIG. 6A

```
43    c ----------------- analysis options ---------------
44    title sc6.i Seal CT-Solid r_t=10mm r_ps=3mm  P_cuff=3.0 990428
45    c
46    c    *** DYNA3D Analysis Options ***
47    c
48    dyna3d
49    dynaopts
50     term 6.5e-2
51     plti 5.e-4
52     prti 2.5e-2
53    c
54    c .... DR options
55    c
56    itrx 500
57    c
58    c .... increase DR tol to prevent convergence after compression before expansion
59    c
60    c tolrx 1.0e-6
61    tolrx 1.0e-12
62    drdb
63    c
64     tssf 0.9
65    c
66    c .... turn off (0) or on (1) SAND database flag
67    c
68      edsdf 0
69    c
70     nrest 90000
71     nrunr  5000 ;
72    c
73    c .... symmetry planes on xz and yz planes
74    c
75    plane 1
76      0.0 0.0 0.0
77      1.0 0.0 0.0    0.001    symm ;
78    plane 2
79      0.0 0.0 0.0
80      0.0 1.0 0.0    0.001    symm ;
81    c
82    c .... DYNA3D slidesurface: +x folder cylinder
83    c
84    sid 1 sv
```

FIG. 6B

```
85    pnlts 1.0
86    pnltm 1.0
87    pen
88    ;
89    c
90    c .... DYNA3D slidesurface: -x folder cylinder
91    c
92    sid 2 sv
93    pnlts 1.0
94    pnltm 1.0
95    pen
96    ;
97    c
98    c
99    c .... DYNA3D slidesurface: +y folder cylinder
100   c
101   sid 3 sv
102   pnlts 1.0
103   pnltm 1.0
104   pen
105   ;
106   c
107   c .... DYNA3D slidesurface: -y folder cylinder
108   c
109   sid 4 sv
110   pnlts 1.0
111   pnltm 1.0
112   pen
113   ;
114   c
115   c .... DYNA3D tpeg to aorta (aorta is master)
116   c
117   sid 5 sv
118   c
119   c .... solid element aorta
120   c
121   pnlts 0.1
122   pnltm 0.1
123   c
124   c .... shell element aorta
125   c
126   c pnlts 1.0
```

```
127  c pnltm 1.0
128  pen
129  ;
130  c
131  c .... load curve:  hemodynamics  **** ADD DR FLAG TO INPUT FILE ****
132  c
133  lcd 1
134      0.000E+00              0.000E+00
135      [%t_init+2*%t_fold+1.0e-3]  0.000e+00
136      [%t_init+2*%t_fold+2.0e-3]  %P_hemo
137      1.000E+00              %P_hemo ;
138  c
139  c .... load curve:  channel !! NOT USED !! **** ADD DR FLAG TO INPUT FILE ****
140  c
141  lcd 2
142      0.000E+00 0.000E+00
143      [%t_init+2*%t_fold+1.0e-3]  0.000e+00
144      [%t_init+2*%t_fold+2.0e-3]  0.000e-00
145      1.000E+00              0.000e-00 ;
146  c
147  c .... load curve:  proximal cuff **** ADD DR FLAG TO INPUT FILE ****
148  c
149  lcd 3
150      0.000E+00 0.000E+00
151      [%t_init+2*%t_fold+1.0e-3]  0.000e+00
152      [%t_init+2*%t_fold+2.0e-3]  %P_cuff
153      1.000E+00              %P_cuff ;
154  c
155  c .... load curve for +x folder cylinder motion/velocity
156  c
157  lcd 4
158      0.000E+00              0.000E+00
159      %t_init                0.000E+00
160      [%t_init+1.0E-04]      [-%vel_fold]
161      [%t_init+%t_fold]      [-%vel_fold]
162      [%t_init+%t_fold+1.0e-3]   0.000E+00
163      [%t_init+2*%t_fold+1.0e-3] 0.000e+00
164      [%t_init+2*%t_fold+2.0e-3] [2.0*%vel_fold]
165      [%t_init+3*%t_fold+2.0e-3] [2.0*%vel_fold]
166      [%t_init+3*%t_fold+3.0e-3] 0.000e+00
167      1.000E+00       0.000E+00 ;
168  c
```

FIG. 6E

```
169    c .... load curve for -x folder cylinder motion
170    c
171    lcd 5
172       0.000E+00                0.000E+00
173       %t_init                  0.000E+00
174       [%t_init+1.000E-04]      [ %vel_fold]
175       [%t_init+%t_fold]        [ %vel_fold]
176       [%t_init+%t_fold+1.0e-3]    0.000E+00
177       [%t_init+2*%t_fold+1.0e-3]  0.000e+00
178       [%t_init+2*%t_fold+2.0e-3]  [-2.0*%vel_fold]
179       [%t_init+3*%t_fold+2.0e-3]  [-2.0*%vel_fold]
180       [%t_init+3*%t_fold+3.0e-3]  0.000e+00
181       1.000E+00                0.000E+00 ;
182    c
183    c .... load curve for +y folder cylinder motion
184    c
185    lcd 6
186       0.000E+00                0.000E+00
187       %t_init                  0.000E+00
188       [%t_init+1.000E-04]      [-%vel_fold]
189       [%t_init+%t_fold]        [-%vel_fold]
190       [%t_init+%t_fold+1.0e-3]    0.000E+00
191       [%t_init+2*%t_fold+1.0e-3]  0.000e+00
192       [%t_init+2*%t_fold+2.0e-3]  [2.0*%vel_fold]
193       [%t_init+3*%t_fold+2.0e-3]  [2.0*%vel_fold]
194       [%t_init+3*%t_fold+3.0e-3]  0.000e+00
195       1.000E+00                0.000E+00 ;
196    c
197    c .... load curve for -y folder cylinder velocity
198    c
199    lcd 7
200       0.000E+00                0.000E+00
201       %t_init                  0.000E+00
202       [%t_init+1.000E-04]      [ %vel_fold]
203       [%t_init+%t_fold]        [ %vel_fold]
204       [%t_init+%t_fold+1.0e-3]    0.000E+00
205       [%t_init+2*%t_fold+1.0e-3]  0.000e+00
206       [%t_init+2*%t_fold+2.0e-3]  [-2.0*%vel_fold]
207       [%t_init+3*%t_fold+2.0e-3]  [-2.0*%vel_fold]
208       [%t_init+3*%t_fold+3.0e-3]  0.000e+00
209       1.000E+00                0.000E+00 ;
210    c
```

```
211   c ----------------- parts and materials -----------------
212   c
213   c
214   c .... get CT-data meshed aorta; convert cm to inches
215   c
216   csca [1./2.54]
217   include tpeg.part_ct_aorta3
218   c
219   csca 1.0
220   c
221   c .... option for analytical aorta model
222   c
223   c include tpeg.part_eq_aorta
224   c
225   include tpeg.part_cuff1
226   include tpeg.part_folder2
227   c
228   include tpeg.materials_dyna
229   c
230   c .... use negative tols to prevent aorta nodes merging w/ folder cylinder
231   c      nodes if they coincidently become adjacent
232   c
233   c .... merge nodes within CT aorta part using rather loose tolerance
234   c
235   bptol 1 1 0.01
236   bptol 1 3 -1.0
237   bptol 1 4 -1.0
238   bptol 1 5 -1.0
239   bptol 1 6 -1.0
240   tp .001
241   c
```

```
1    c
2    c         tpeg.part_ct_aorta3
3    c            April 15, 1999
4    c
5    c ------- Aortic Model for Inflatable TPEG Model ---------
6    c         Derived from Patient CT Data
7    c         Outer surface constructed with 0.52 mm offset from inner
8    c
9    c .... this is an aortic mesh file which surrounds the neck of the
10   c     3-D AAA reconstruction with solid elements.
11   c
12   c     This file uses TrueGrid planes, oriented by eye using trial
13   c     and error graphically, to determine an orthonormal section.
14   c     Trick there is to adjust surface until walls of proximal neck section
15   c     are parallel to global z axis. Use rz to rotate screen to find values,
16   c     then use in surface transformation to position CT data for meshing.
17   c
18   c .... import IGES file containing surface data from CT scan
19   c
20   iges solid1.igs 1 1 mx -18.54 my -16.8    ry 24 rx 22 mz 4.8;
21   c
22   c .... inner surface
23   c
24   sd 17 sds 9 12;
25   c
26   c .... outer surface
27   c
28   sd 18 sds 15 16 ;
29   c
30   sd 201 plan
31         0. 0. 1.5
32         0 0 1
33   sd 202 plan
34         0. 0. 2.5
35         0 0 1
36   sd 203 plan
37         0. 0. -2.3
38         0 0 1
39   sd 204 plan
40         0. 0. 3.3
41         0 0 1
42   sd 301 cy 0 0 0 0 0 1 1.35
```

```
43      sd 401 plan
44         0. 0. 0.
45         0. 1. 0.
46      c
47      c .... adjust mz to position part at cuff on Z-axis;
48      c        cuff may be z=[2,2.15]
49      cylinder
50        1 2;
51      1 2 3;
52      1 2 3 4 ;
53      c
54      1.0 1.25
55      0 180.0 360.0
56      -2.3 1.5 2.5 3.3
57      c
58      mseq i 2
59      mseq j 29 29
60      mseq k 20 5 5
61      c
62      c .... project top and bottom ends of aorta segment onto orthonormal planes
63      c
64      sfi ; ; -2;  sd 201
65      sfi ; ; -3;  sd 202
66      c
67      c .... project top of upper neck segment onto orthonormal plane
68      c
69      sfi ; ; -4;  sd 204
70      c
71      c .... project bottom of lower neck segment onto orthonormal plane
72      c      after radially expanding bottom ring by delta-r=2.0
73      mbi -1; ; -1; x 2.0
74      mbi -2; ; -1; x 2.0
75      sfi ; ; -1;  sd 203
76      c
77      c .... project inner cylinder surface onto aorta luminal surface
78      c
79      sfi -1; 1 3; 2 3; sd 17
80      sfi -1; 1 3; 3 4; sd 17
81      sfi -1; 1 3; 1 2; sd 17
82      c
83      c .... project outer cylinder onto aorta outer wall surface
84      c
```

```
85      sfi -2; 1 3; 2 3; sd 18
86      sfi -2; 1 3; 3 4; sd 18
87      sfi -2; 1 3; 1 2; sd 18
88      c
89      c .... project theta=0/360 seam onto a plane to facilitate merging
90      c
91      sfi 1 2; -1; ; sd 401
92      sfi 1 2; -3; ; sd 401
93      c
94      c
95      c ... --- slidesurface definition with TPEG body ---
96      c
97      orpt + 0. 0. 3.0
98      sii -1; 1 3; 3 4;  5 m
99      c
100     c .... +y hemicylinder is material 11; -y is mat 12
101     c
102     mti ; 1 2; 2 4 ;  11
103     mti ; 2 3; 2 4;  12
104     c
105     c .... rigid material for aneurysm sac
106     c
107     mti ; 1 3; 1 2;  13
108     c
109     c .... Boundary Conditions
110     c    * fix proximal end only in z
111     c
112     bi ; ; -4; dz 1 ;
113     c
114     c .... adjust mz to position aorta at cuff on Z-axis;
115     c       cuff may be z=[2,2.15]
116     lct 1
117        mz [1.01*2.54] mx 0.7; ;
118     lrep 1 ;
119     endpart
120     c
```

FIG. 8A

```
1    c ****** Slotted Tube Integrated Stent Design Simulation *******
2    c              (istent.run)
3    c       Stent design analysis & CT-Anatomy simulation
4    c
5    c ------------------ parameter settings ------------------
6    c
7    c .... inike=1 => make nike file; inike=0 => make dyna file
8    c .... imodel = 0 => full 3 segment model with interconnects
9    c           = 1 => 3-crown segment only
10   c           = 2 => 6-crown segment only
11   c           = 3 => 12-crown segment only
12   c .... isym = 0 => full 360 deg model
13   c           = 1 => symmetric model
14   c .... isim_mode:  type of simulation
15   c        = 1: => radial force to R_f = 80% R_0, restoring stress mat'l
16   c        = 2: => flat plate force, restoring stress mat'l
17   c        = 3: => predelivery compression to 12 F, loading stress mat'l
18   c        = 4: => initial expansion
19   c        = 5: => frequency analysis
20   c        = 6: => anatomy deployment
21   c .... refine = X => add X elements via mseq in each direction
22   c                of the cross section
23   c
24   c !!! warning - only 1st 8 characters of variable unique !!!!
25   c
26   parameter inike 1 ;
27   parameter imodel 2 ;
28   parameter isym 0 ;
29   parameter isim_mode 6 ;
30   parameter refine 1 ;
31   c
32   para Tighten [0.9];    c helps 'tighten' or stiffen spline
33                          c range (0.5,1) (probably should not change)
34   c
35   c ------------------ parameter settings ------------------
36   c
37   c .... ========== design parameters ==========
38   c
39   c Note: Adjust specified OD for each segment considering the wall thickness
40   c       for that segment so that ID's match in a consistent way for the
41   c       tube blank from which they were cut.
42   c
43   c Upper segment --- 3 crowns
44   c Middle segment -- 6 crowns
45   c Lower segment --- 12 crowns (could be conical)
46   c
47   c Parameters for 3-crown segment
48   c
49   para
```

FIG. 8B

```
50      RCyl3 [29*0.5/25.4]
51          dCIA3 [-.00]  c delta of center of inner arc for 3 crown segment (-:0)
52          dCOA3 [0]     c delta of center of outer arc for 3 crown segment (0:+)
53          CW3 [.020]    c Circumferential width of segments for 3 crowns
54          RW3 [.018]    c Radial width for 3 crowns
55          NRA3 [.0195]  c normal radius of smaller cylinders (arcs)
56                        c for 3 crowns
57          Ht3 [1.048]   c distance from center of upper arcs
58                        c to center of lower arcs for 3 crowns
59          NLegEl3 [12]; c number of elements along the leg
60      c
61      c Parameters for 6-crown segment
62      c
63      para
64          RCyl6 [29*0.5/25.4]  c outside radius for 6 crown segment
65          dCIA6 [0]     c delta of center of inner (smaller) arc for 6 crown segment (-:0)
66          dCOA6 [0.005] c delta of center of outer (larger) arc for 6 crown segment (0:+)
67          CW6 [.020]    c Circumferential width of segments for 6 crowns
68          RW6 [.018]    c Radial width for 6 crowns
69          NRA6 [.0195]  c normal radius of smaller cylinders (arcs)
70                        c for 6 crowns
71          Ht6 [.310]    c distance from center of upper arcs
72                        c to center of lower arcs for 6 crowns
73          NLegEl6 [12]; c number of elements along the leg
74      c
75      c Parameters for 12-crown segment
76      c
77      para
78          dCIA12 [0]    c delta of center of inner arc for 12 crown segment (-:0)
79          dCOA12 [0]    c delta of center of outer arc for 12 crown segment (0:+)
80          CW12 [.008]   c Circumferential width of segments for 12 crowns
81          RW12 [.008]   c Radial width for 12 crowns
82          NRA12 [.006]  c normal radius of smaller cylinders (arcs)
83                        c for 12 crowns
84          Ht12 [.164]   c distance from center of upper arcs
85                        c to center of lower arcs for 12 crowns
86                        c (measured along the leg, not necessarily in
87                        c the z direction)
88          c first outside radius for 12 crown segment (near other segments)
89          RCyl12_1 [22*0.5/25.4]
90          c second outside radius for 12 crown segment (bottom)
91          RCYl12_2 [20*0.5/25.4]
92      c
93          NLegEl12 [10]; c number of elements along the leg
94      c
95      c Interconnects
96      c
97      c Upper interconnects
98      c
```

```
99      para
100     c   HIUp    [.10]   c height of interconnect
101         HIUp    [.20]   c height of interconnect
102         FRUp    [.016]  c fillet radius for blend
103         ICWUp   [.010]  c circumferential width
104         IRWUp3  [.016]  c radial width at 3-crown end
105         IRWUp6  [.016]; c radial width at 6-crown end
106     c
107     c S-interconnects
108     c
109     para
110     c   SIVer [.03]     c vertical distance between upper or lower arc centers
111         SIVer [.06]     c vertical distance between upper or lower arc centers
112                         c also the distance from the vertical mid-line to
113                         c the first arc center
114         SIHor [.0125]   c horizontal distance between upper two or
115                         c lower two arc centers
116         SIr   [.008]    c arc radius
117         SIrO  [%SIr+%ICWUp/2]  c outer radius
118         SIrI  [%SIr-%ICWUp/2]; c inner radius
119     c
120     c Lower interconnects
121     para
122     c   HILr    [.071]  c height of interconnect
123         HILr    [.142]  c height of interconnect
124         FRLr    [.016]  c fillet radius for blend
125         ICWLr   [.016]  c circumferential width
126         IRWLr6  [.005]  c radial width at 6-crown end
127         IRWLr12 [.005]; c radial width at 12-crown end
128     c
129     c .... ========= design parameters =========
130     c
131     c .... set cylinder ID & OD for compression
132     c
133     if (%isim_mode.le.3.or.%isim_mode.eq.6) then
134     parameter ricompcyl [1.1*max(%RCyl3,%RCyl6,%RCyl12_1,%RCyl12_2)] ;
135     parameter rocompcyl [1.4*max(%RCyl3,%RCyl6,%RCyl12_1,%RCyl12_2)] ;
136     c
137     c .... set cylinder ID & OD for expansion
138     c
139     elseif (%isim_mode.eq.4) then
140     parameter rocompcyl [0.95*(min(%RCyl3,%RCyl6,%RCyl12_1,%RCyl12_2)-%RW6)] ;
141     parameter ricompcyl [0.7* (min(%RCyl3,%RCyl6,%RCyl12_1,%RCyl12_2)-%RW6)] ;
142     endif
143     c
144     c Materials assignments
145     c
146     parameter matst12 3 ;
147     parameter matst6  4 ;
```

FIG. 8C

```
148     parameter matst3  5 ;
149     parameter mati126 6 ;
150     parameter mati63  7 ;
151     c
152     if (%isim_mode.eq.1) then
153         echo *** Radial Force Simulation ***
154     elseif (%isim_mode.eq.2) then
155         echo *** Flat Plate Force Simulation ***
156     elseif (%isim_mode.eq.3) then
157         echo *** Predelivery Compression Simulation ***
158     elseif (%isim_mode.eq.4) then
159         echo *** Initial Expansion Simulation ***
160     elseif (%isim_mode.eq.5) then
161         echo *** Natural Frequency Analysis ***
162     elseif (%isim_mode.eq.6) then
163         echo *** Anatomy Deployment Simulation***
164     else
165         echo !!! ERROR: illegal isim_mode !!!
166         interrupt
167     endif
168     c
169     c ————————— analysis options —————————
170     title human-size stent anatomy deployment
171     c
172     c    *** DYNA3D Analysis Options ***
173     c
174     if (%inike.eq.0) then
175       echo Making DYNA3D input file
176       dyna3d
177         dynaopts
178         term 2.0e-4
179         plti 1.e-4
180         prti 5.0e-6
181     c
182     c .... DR options
183     c
184     c itrx 500
185     c tolrx 1.0e-6
186     c drdb
187     c
188     c .... thermal effects option - temp from load curve 1
189     c
190     if (%isim_mode.ne.5) then
191         teo 1
192     endif
193     c
194         tssf 0.0
195     c
196     c print initial time step size
```

```
197  c
198  c prtflg 1
199  c
200  c .... turn off (0) or on (1) SAND database flag
201  c
202    edsdf 0
203  c
204    nrest 90000
205     nrunr 95000 ;
206  c
207  c .... DYNA3D stent to compression cyl
208  c
209    sid 1 dni
210  c sfif
211  c mfif
212    pnlts 1.0e-0
213    pultm 1.0e-0
214     ;
215  c
216  c .... DYNA3D tied interface to interconnects if multisegment
217  c
218  if (%imodel.eq.0) then
219    sid 2 tied
220     ;
221  endif
222  c
223  c .... end DYNA3D commands
224  c
225  endif
226  c
227  c    *** NIKE3D Analysis Options ***
228  c
229  if (%inike.eq.1) then
230    echo Making NIKE3D input file . . .
231    nike3d
232    nikeopts
233  c
234  c .... temperatures follow load curve 1
235  c   ** manually add tref=1.0 on matl 2 control card cols 26-35 **
236  c
237    tco 1
238  c
239  if (%isim_mode.eq.5) then
240    anal dyn
241    neig 20
242    shift 69
243    iplt 1
244    nsbrr 1
245    stifcore 1
```

FIG. 8F

```
246      bfgscore
247      bwmo new
248    c
249    c  element constitutive data incore
250    c
251      bfor 10
252      sfor 10
253      bef 11
254    c
255    c .... linear solver
256    c
257      lsolver fissle
258    c
259    elseif (%isim_mode.ne.5) then
260    c
261    c .... time step analysis
262    c
263      nstep 100
264      delt 0.0100
265      anal stat
266    c
267    c .... step tol of 1e-2 is OK for predel compression
268    c
269    if (%isim_mode.eq.1.or.%isim_mode.eq.2) then
270      dctol -1.0e-3
271    elseif (%isim_mode.eq.3) then
272      dctol -1.0e-2
273    endif
274    c
275    c .... max iterations per stiffness reform
276    c
277      nibsr 20
278    c
279    c .... max stiffness reforms per step
280    c
281      msrf 20 ;
282    if (%isim_mode.eq.1.or.%isim_mode.eq.2) then
283      iprt 1
284    elseif (%isim_mode.eq.3.or.%isim_mode.eq.4) then
285      iprt 25
286    endif
287      iplt 1
288      nsbrr 1
289      stifcore 1
290      bfgscore
291      bwmo new
292      echo Bandwidth minimization ACTIVATED with "NEW" option
293    c
294    c element constitutive data incore
```

FIG. 8G

```
295  c
296     bfor 10
297     sfor 10
298     bef 11
299  c
300  c .... linear solver
301  c
302     lsolver fissle
303  c
304  c .... solid element stent contact surface
305  c
306  sid 1 sv
307  c
308  if (%isim_mode.eq.1) then
309  c
310  c .... below changed for sharp-edge laser-cut stent
311  c
312     pnlt 1.0e-3
313  elseif (%isim_mode.eq.2) then
314     pnlt 0.01
315  elseif (%isim_mode.eq.3) then
316  c
317  c .... essential to cut penalty for laser-cut stent predel compression
318  c
319  pnlt 0.001
320  elseif (%isim_mode.eq.4) then
321     pnlt 1.0e-3
322  c iaug 1 ;
323  endif
324     ;
325  c
326  c .... end block for time step only analysis
327  c
328  endif
329  c
330  c .... slidesurface between interconnects and segments
331  c
332  sid 2 tied
333     ;
334  c
335  c .... slidesurface between stent and aortic wall
336  c
337  if (%isim_mode.eq.6) then
338  echo *** Add activation time of 0.5 to slidesurface 2 ***
339  sid 3 sv
340  ;
341  endif
342  c
343  c .... NIKE3D shell geometric stiffness (HL only)
```

FIG. 8H

```
344    c
345      segs 1 ;
346    c
347    c .... end NIKE3D section
348    c
349    endif
350    c
351    c .... symmetry planes (omit for freq analysis)
352    c
353    if (%isim_mode.ne.5) then
354    if (%isym.eq.1) then
355    c
356    c .... Symmetric Model
357    c
358    c plane 1
359    c   0.0 0.0 0.0
360    c   [-sin(60)] [-cos(60)] 0.0
361    c     0.0005 symm ;
362    c plane 2
363    c   0.0 0.0 0.0
364    c   [-sin(60)] [cos(60)] 0.0
365    c     0.0005 symm ;
366    c
367    else
368    c
369    c .... symmetry planes to remove rigid body modes for full model
370    c
371    plane 1
372      0.0 0.0 0.0
373      1.0 0.0 0.0
374       .0005 symm ;
375    plane 2
376      0.0 0.0 0.0
377      0.0 1.0 0.0
378       .0005 symm ;
379    endif
380    endif
381    c
382    c
383    if (%inike.eq.0) then
384    c
385    c .... Load Curves for DYNA3D  **** ADD DR FLAG TO INPUT FILE ****
386    c
387    if (%isim_mode.eq.1) then
388    c
389    c .... radial force
390    c
391    lcd 1
392        0.000E+00 1.000E+00
```

```
393          7.500E-03 2.250E+02
394          1.000E-00 2.250E+02 ;
395      elseif (%isim_mode.eq.2) then
396      c
397      c .... flat plate compression, lcd 1 not used (dummy definition)
398      c
399      echo !!! Flat plate not implemented for DYNA3D !!!
400      quit
401      c
402      elseif (%isim_mode.eq.3) then
403      c
404      c .... predelivery compression strain - 0.87 in. dia compressed to 12F
405      c      [check x-displ of stent center node to verify]
406      c
407      lcd 1
408          0.000E+00 1.000E+00
409          1.000E-02 1.008E+03
410          1.000E-00 1.008E+03 ;
411      elseif (%isim_mode.eq.6) then
412      c
413      c .... anatomy deployment
414      c     (LC from radial comp)
415      c
416      lcd 1
417          0.000E+00 1.000E+00
418          7.500E-04 1.000E+03
419          9.000E-04 1.000E+03
420          1.500E-03 1.000E+00
421          1.000E-00 1.000E+00 ;
422      endif
423      c
424      c .... load curve #2 only used for flat plate compression
425      c
426      lcd 2
427          0.000E+00 0.000E+00
428          1.000E+00 0.000e-00 ;
429      endif
430      c
431      if (%inike.eq.1) then
432      c
433      c .... ******** Load Curves for NIKE3D **********
434      c
435      if (%isim_mode.eq.1) then
436      c
437      c .... radial force
438      c
439      lcd 1
440          0.000E+00 1.000E+00
441          1.000E+00 3.000E+02 ;
```

```
442      elseif (%isim_mode.eq.2) then
443      c
444      c .... flat plate compression, lcd 1 not used (dummy definition)
445      c
446      lcd 1
447          0.000E+00 1.000E+00
448          1.000E+00 0.000E+00 ;
449      elseif (%isim_mode.eq.3) then
450      c
451      c .... predelivery compression strain - 0.87 in. dia compressed to 12F
452      c      [check x-displ of stent center node to verify]
453      c
454      lcd 1
455          0.000E+00 1.000E+00
456          1.000E+00 1.008E+03 ;
457      elseif (%isim_mode.eq.4) then
458      c
459      c .... initial expansion strain - 4/5 mm OD to 15/27 mm OD
460      c      [check x-displ of stent center node to verify]
461      c
462      lcd 1
463      c .... thermal load (activate TEO above)
464          0.000E+00 1.000E+00
465          1.000E+00 -1.008E+03 ;
466      c .... prescribed displacement
467      c   0.000E+00 0.000E+00
468      c   1.000E+00 1.000E-01 ;
469      c
470      elseif (%isim_mode.eq.5) then
471      c
472      c .... must define load curve since TEO active even if unused for freq
473      c
474      c .... initial expansion strain - 4/5 mm OD to 15/27 mm OD
475      c      [check x-displ of stent center node to verify]
476      c
477      lcd 1
478      c .... thermal load (activate TEO above)
479          0.000E+00 1.000E+00
480          1.000E+00 -1.008E+03 ;
481      elseif (%isim_mode.eq.6) then
482      c
483      c .... anatomy deployment - 0.87 in. dia compressed to 12F
484      c
485      lcd 1
486          0.000E+00 1.000E+00
487          0.500E+00 5.000E+02
488          1.000E+00 1.000E+00 ;
489      endif
490      endif
```

FIG. 8K

```
491  c
492  c ------------------ stent parts ------------------
493  c
494  include irss.tg
495  c
496  c ------------------ anatomy parts ------------------
497  c
498  if (%isim_mode.eq.6) then
499  c
500  c .... convert anatomy data from cm to inch units
501  c
502  control
503  csca [1./2.54]
504  c
505  c .... import meshed anatomy data for stent deployment
506  c        (this is an aortic stent)
507  c
508  include tpeg.part_ct_aorta3
509  csca 1.0
510  merge
511  if (%inike.eq.1) then
512  c
513  c .... set material properties for aortic wall
514  c
515  include aorta.materials_nike
516  endif
517  endif
518  c
519  c ------------------ stent materials ------------------
520  c
521  if (%inike.eq.1) then
522       if (%isim_mode.eq.1.or.%isim_mode.eq.2) then
523          include istent.mats_nike_solid
524          echo  NiTi model for radial force/flat plate analysis
525       elseif (%isim_mode.eq.3) then
526          include istent.mats_compress_nike_solid
527          echo  NiTi model for predelivery compression strain
528       elseif (%isim_mode.eq.4) then
529          include istent.mats_compress_nike_solid
530          echo  NiTi model for initial expansion strain
531       elseif (%isim_mode.eq.5) then
532          include istent.mats_nike_freq_solid
533          echo  NiTi model for frequency analysis
534       elseif (%isim_mode.eq.6) then
535          include istent.mats_nike_solid
536          echo  NiTi model for anatomy deployment
537       endif
538  c
539  elseif (%inike.eq.0) then
```

FIG. 8L

```
540      if (%isim_mode.eq.1.or.%isim_mode.eq.2) then
541         include istent.mats_dyna_solid
542         echo  NiTi model for radial force/flat plate analysis
543      elseif (%isim_mode.eq.3) then
544         include istent.mats_compress_dyna_solid
545         echo  NiTi model for predelivery compression strain
546      elseif (%isim_mode.eq.4) then
547         include istent.mats_compress_dyna_solid
548         echo  NiTi model for initial expansion strain
549      elseif (%isim_mode.eq.6) then
550         include istent.mats_compress_dyna_solid
551         echo  NiTi model for anatomy deployment
552      endif
553   endif
554   c
555   c .... cylindrical compression for radial force or predelivery compression
556   c
557   if (%isim_mode.eq.1.or.%isim_mode.eq.3.or.%isim_mode.eq.4.or.%isim_mode.eq.6) then
558   c
559      if (%isym.eq.1) then
560         include cylinder.parts_sym
561      else
562         include cylinder.parts
563      endif
564   endif
565   c
566   if (%inike.eq.1) then
567      include cylinder.materials_nike
568   elseif (%inike.eq.0) then
569      include cylinder.materials_dyna
570   endif
571   c
572   stp .0001
573   c
574   c .... Constrain stent node(s) in z-direction for time-hist analysis
575   c
576   if (%isim_mode.ne.5) then
577   merge
578   c
579   c .... nset for 3-segment model
580   c nset zconstr = 1 8149 8687 9215 9747 ;
581   c echo  ** Bottom 12-crown node list Constrained in Z-translation **
582   c
583   c .... nset for 6-crown only
584   echo  ** Bottom 6-crown node list constrained in z-dir **
585   nset zconstr = 1 43 97 151 448 ;
586   b nset zconstr dz 1 ;
587   endif
588   c
```

VIRTUAL PROTOTYPING AND TESTING FOR MEDICAL DEVICE DEVELOPMENT

RELATED PATENT APPLICATIONS

This patent application is a divisional of U.S. patent application Ser. No. 12/904,994, filed Oct. 14, 2010, naming Robert G. Whirley and Michael V. Chobotov as inventors, entitled VIRTUAL PROTOTYPING AND TESTING FOR MEDICAL DEVICE DEVELOPMENT, which is a continuation and claims the benefit of U.S. patent application Ser. No. 09/679,725, filed Oct. 4, 2000, naming Robert G. Whirley and Michael V. Chobotov as inventors, entitled VIRTUAL PROTOTYPING AND TESTING FOR MEDICAL DEVICE DEVELOPMENT, both of which are incorporated by reference herein in their entirety, including all text and drawings.

BACKGROUND

1. Field of the Invention

This invention relates to systems and methods of developing better-designed medical devices, specifically, intracorporeal medical devices and particularly cardiovascular stents and endovascular grafts.

2. Background and Description of Related Art

Atherosclerotic vascular disease is a significant health problem facing the world population today. Atherosclerosis results in two primary types of lesions-occlusive and aneurysmal, with the aorta being the primary site of aneurysmal disease. Occlusive disease is a process in which a vessel lumen becomes narrowed and the blood flow restricted. Occlusive disease is typically associated with plaque buildup on the vessel wall or a biological response to vessel injury. One approach to treatment of occlusive disease involves placing a stent inside the vessel to act as a structural scaffold and hold open the vessel, and also possibly to provide local drug delivery or local radiation treatment. Aneurysmal disease is a process in which a vessel dilates under the influence of hemodynamic pressure, and may ultimately lead to rupture of the vessel and severe internal bleeding. One approach to treatment of aneurysmal disease involves placing a TPEG (transluminally placed endovascular graft, or "stent graft") across the aneurysm, excluding the aneurysm from hemodynamic pressure and thereby reducing or eliminating the risk of rupture. Examples of such grafts can be found in co-pending U.S. patent application Ser. No. 09/133,978, now U.S. Pat. No. 6,395,019, filed Aug. 14, 1998 by Chobotov, which is hereby incorporated by reference herein in its entirety.

A TPEG is an endovascular prosthetic device that lines the interior of an artery to provide flow path integrity and structural support to the damaged or diseased blood vessel. TPEGs are sometimes called "stent grafts" because they were originally created using combinations of stents and synthetic vascular graft segments. TPEGs are delivered to a blood vessel location in a compressed state, through an incision, and are then deployed at the location of concern.

The current development process of TPEGs and medical devices generally, usually involves the reiterative and sequential steps of designing, fabricating the prototype, and testing the prototype until the required performance specifications are met. Fabrication of the prototype entails the building of the actual medical device, e.g., a TPEG. Testing can involve animal testings, human clinical trials, stress, strain, and deformation testing, and the like. Stents, TPEGs and other medical devices have suffered from long development times and from design deficiencies discovered late in the development and testing process. Thus, the development of improved medical devices could be significantly accelerated if design deficiencies could be identified earlier, before committing to lengthy laboratory testing, animal studies, and human clinical trials. A system that enables early evaluation of many aspects of device performance in vivo, and is applicable to development of stents for occlusive disease, TPEGs for aneurysmal disease, and other medical devices is highly desirable.

In designing a TPEG, several factors must be taken into account, such as the structural integrity of the TPEG, the prevention of perigraft leaks, the need for a more easily-controlled TPEG deployment to allow a more precise positioning of the TPEG, the kink resistance of the TPEG, the morphology of the arterial walls, the relatively large size and lack of TPEG flexibility in the undeployed configuration (which can create difficulties in passing the TPEG from its insertion site to its deployment site), and the like. In vivo boundary conditions and forces, particularly dynamic or static cyclic in vivo forces, and the material properties of a TPEG are also important factors. Taking these factors into consideration during virtual testing and development of a medical device generates a more accurate assessment of the maximum stresses, strains, and deformations, over time that may potentially be handled by a medical device such as a TPEG.

In designing a stent, several factors must be considered including radial force, crush resistance, flexibility (in both the compressed and the deployed configurations), fatigue life, and tissue intrusion through open stent cells. A system that allows rapid evaluation of these and other characteristics of a stent design before hardware prototypes are constructed, thereby reducing the cost and time required for development and also expanding the designer's capability to explore more exotic designs and possibly discover new and more advantageous stent designs within a given budget and timeframe is highly desirable.

Thus, systems and methods which allow accurate virtual testing of a medical device design with respect to one or more of the above noted factors, in addition to other factors not specifically enumerated, without the need for an actual prototype of the design, are needed. Such systems and methods can reduce the cost of medical device development and increase the safety and efficacy of the designs.

SUMMARY

The invention provides a system and method for developing better-designed medical devices and particularly cardiovascular stents and endovascular grafts. The system comprises a Geometry Generator, a Mesh Generator, a Stress/Strain/Deformation Analyzer, and, optionally, a Visualization tool. The invention may obtain anatomic data from 3D volumetric data. In other embodiments, the invention utilizes an idealized anatomical feature, an in vitro model, or no anatomical feature at all.

In one embodiment, the Geometry Generator receives three-dimensional volumetric data of an anatomical feature and accordingly extracts the surface points of such data, which in turn is received by the Mesh Generator. In another embodiment, the Geometry Generator based on algorithms available in such Geometry Generator software generates an output that is directly received by the Mesh Generator. Using the output generated by the Geometry generator and the geometric model of a candidate medical device, the Mesh Generator generates a mesh or a finite element model incorporating either the anatomical feature or in vitro model and candidate medical device. In an embodiment where no anatomical feature is used, a mesh only incorporating the candidate medical device is generated. The Stress/Strain/Deformation Analyzer then receives the mesh and the material models, the loads and/or displacements placed on the anatomical feature or in vitro model, if applicable, and the candidate medical device. Using stress and strain deformation analysis, particularly non-linear analysis, the Stress/Strain/Deformation Analyzer simulates and analyzes the potential in vivo stresses, strains, and deformations or motions of the candidate medical device. Such strains, stresses, and deformations may optionally be displayed using a Visualization tool.

Various embodiments of the invention can be used to provide a variety of useful functions and capabilities to those who design, manufacture and use medical devices. Specifically, embodiments of the invention may be used to model anatomical features or anatomical environments dynamically. As a result, a computer generated model of a medical device, or the like, may be virtually placed or deployed within the anatomical model to measure the response of the device to the environment. The dynamics of the computer generated model of the anatomical features or environment can be accelerated dramatically such that large numbers of normal biological cycle, such as a heartbeat, can be imposed upon the computer generated medical device model in a relatively short period of time.

This gives medical device designers the ability to virtually test a proposed design in a short period of time relative to the time it would take for a similar number of dynamic biological cycles in vivo. Thus, the iterative process of device design and testing of designs is accelerated and improvements in medical device technology can be achieved at a quicker rate. Further, embodiments of the invention can be used to vary and test material properties of medical device components over a broad range in a short period of time using the non-linear modeling capabilities of the embodiments. This capability can be used to select materials having optimal properties for producing the safest and most efficacious designs within a given set of design parameters.

Another benefit of embodiments of the invention is directed to varying material and configuration properties of models of anatomical features such that a simulation of testing of a given device could be performed in a large number of patients, as might be carried out in a large scale clinical trial. If the statistical variation of tissue parameters of a given anatomical feature is known for a given patient population, a medical device model could be tested in anatomical models which vary over such a given range. In this way, a large scale clinical trial could be modeled with embodiments of the invention, at least as to certain performance parameters, without the need for large numbers of actual patients being subjected to clinical testing. The data generated from such a clinical trial modeling exercise could be used to produce or refine the design of a medical device such that it performs optimally over a broad range of anatomical environments. The design could be refined using such data to improve robustness and adaptability of the medical device design.

Also, it is possible to use embodiments of the invention to identify failure modes of given medical device designs when such designs are subjected to dynamic mechanical and chemical forces. By identifying the cause of failure in a design, the "weak link" in the design can be pinpointed and necessary corrections to materials or configuration made in order to obviate the problem. It is also possible to test theories of failure experienced during in vivo clinical testing using embodiments of the invention. In other words, if an in vivo clinical failure of a medical device should occur, there may be one or more theories postulated as to the cause of the failure, particularly in a situation where multiple components of a device have failed and it is not clear from the clinical data which failure occurred first, or if an initial failure of one component of the device precipitated subsequent failure of other components of the device. The dynamic modeling capabilities of embodiments of the invention can allow rapid testing of multiple theories as to the timing and causation of complex failure modes and quickly determine which of the postulated theories is correct.

In addition, the dynamic, non-linear analysis modeling capabilities of embodiments of the invention allow a physician, who is responsible for use or implementation of a medical device, to more accurately choose a proper size or type of medical device based on a specific patient's anatomy. Such is the case when a specific patient's anatomy or anatomical feature is substantially duplicated by a computer model of an embodiment of the invention generated from 3-D volumetric image data, or the like. A large number of sizes or types of virtual medical devices can then be placed and tested within the patient's specific anatomical feature to determine optimum safety and efficacy of the design choice.

BRIEF DESCRIPTION OF THE DRAWINGS

FIGS. 5A-5M contain an exemplary text of a command file that is read by a Mesh Generator, such as TRUEGRID, to conduct a component-level analysis of a stent, without the option for simulating deployment into CT-based anatomy.

FIGS. 6A-6F contain an exemplary text of a command file read by TRUEGRID for a simulated TPEG graft deployment in a proximal aortic neck to generate a mesh incorporating both an anatomical feature and medical device and to output files that are read by a Stress/Strain/Deformation Analyzer.

FIGS. 7A-7C contain an exemplary include file used by the command file listed in FIGS. 6A-6F.

FIGS. 8A-8L contain another exemplary command file read by TRUEGRID used in the virtual prototyping system of the present invention for simulating stent deployment into an anatomy from CT data, as opposed to a stent graft deployment.

DETAILED DESCRIPTION

The following detailed description illustrates an embodiment of the invention by way of example, not by way of limitation of the principles of the invention. Various embodiments of the invention will be described by way of illustration with reference to various software tools, but it should be understood that other software tools that have a comparable capabilities of the mentioned tools may be used and other medical device aside from TPEGs may also be developed using this invention. In addition, although the invention is discussed in the context of prosthesis and specifically endovascular grafts, this is in no way meant to limit the scope of the invention.

Systems and methods of embodiments of the invention are suitable for the development and testing of medical devices including those for therapeutic, diagnostic, monitoring and the like purposes. In general, any device that interacts inside a patient's body may be better developed and tested with the systems and methods of embodiments of the present invention.

Embodiments of the present invention are also well suited for development and testing of intracorporeal devices or prosthesis that generally have an acute interaction with anatomical features of a patent. A list of such devices, which is in no way exhaustive, could include endovascular grafts, stents, pacemakers, artificial joints, artificial tendons, heart valves, artificial limbs, orthopedic hardware, surgical equipment such as sutures, staples, etc., and the like.

Embodiments of the present inventions are particularly well suited for the development and testing of devices for use in the vascular system or other bodily systems that have stresses, strains, and deformations which are dynamic, or quasi-static, and cyclic in nature, e.g., the rhythmic pulsing of the arterial system resulting from variations in blood pressure from the patent's beating heart and the resulting cyclic dynamic or quasi-static stresses, strains, and deformations these variations impart on the patient's arteries and medical devices disposed therein or thereon.

Embodiments of the present invention are also suitable for development and testing of interventional medical devices, which have only transient or temporary contact with the anatomical features of a patient. Illustrative examples of such devices can include catheters, balloons, atherectomy devices, guidewires, and the like.

Figure 1:
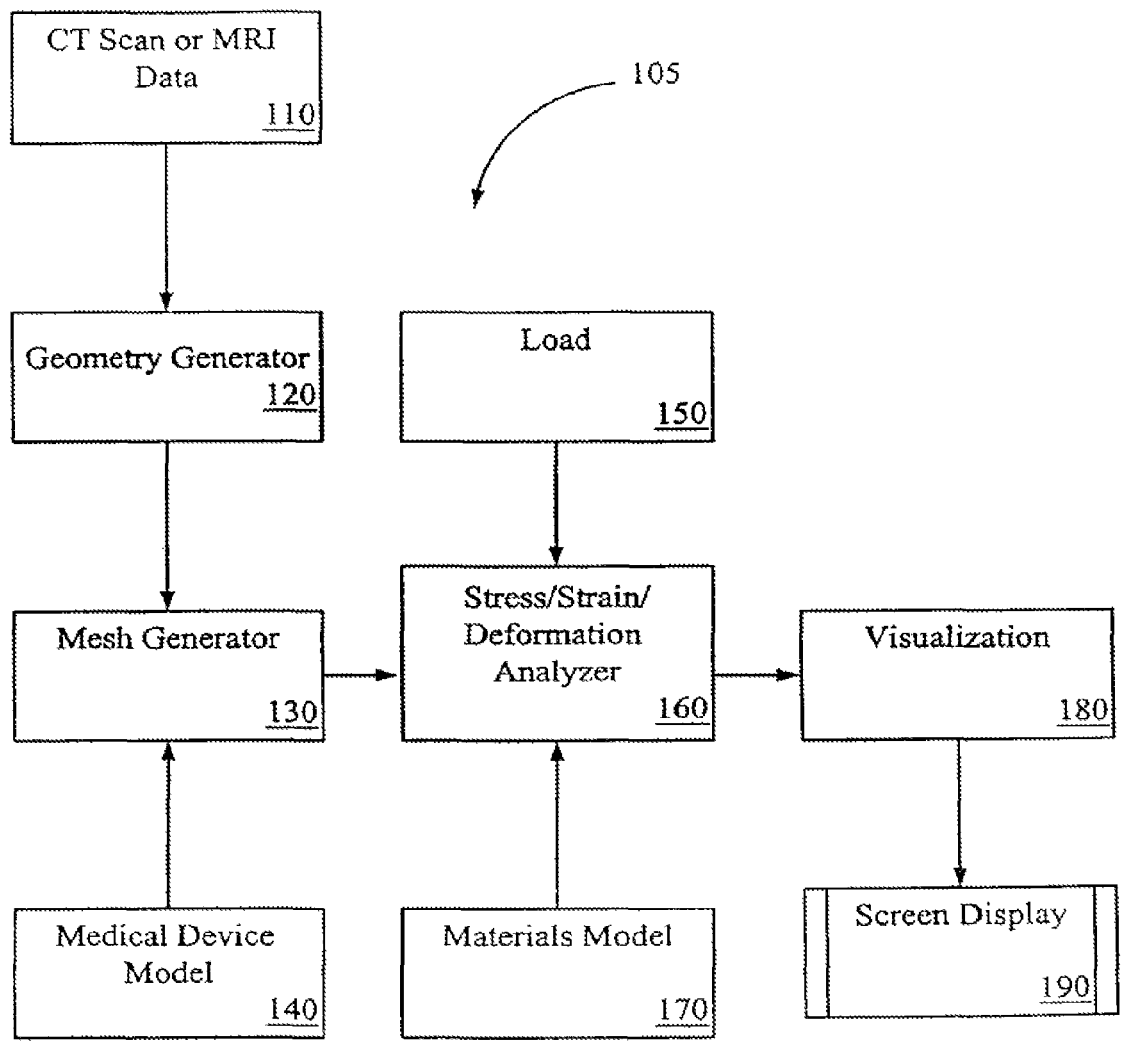
FIG. 1 illustrates a block diagram representation of a virtual prototyping system having features of the present invention.

FIG. 1 is a block diagram showing one embodiment of a virtual prototyping system 105 for analyzing the use of a medical device constructed in accordance with an embodiment of the present invention. FIG. 1 shows that a Geometry Generator 120 receives CT scan or MRI Data 110 as input. The Geometry Generator 120 then processes the CT scan or MRI data and outputs data, which are then received by the Mesh Generator 130 as input. The Mesh Generator, in addition to receiving the output of the Geometry Generator 120, also receives a Medical Device Model data 140 as input. The Medical Device Model 140 contains the geometry (geometric shape or geometric model) of the candidate medical device. Such model may be the complete candidate, a portion, or an element of the candidate medical device. Similarly, a portion or an element of the anatomical features, not the entire anatomy scanned, may be received by the Mesh Generator 130. The Medical Device Model may be created by a computer-aided-design (CAD) software application and stored as a CAD data file. Examples of suitable CAD software packages include I-DEAS (available from SDRC, Inc. of Milford, Ohio) and CATIA (available from International Business Machines Corporation), however, any other suitable application could be used. The Medical Device Model could also, for example, be created through contact or non-contact three dimensional measurement/imaging of a physical device or model. In another embodiment, the medical device model 140 is created within the Mesh Generator 130 module itself.

In addition, although the embodiment of FIG. 1 contemplates the use of CT or MRI volumetric data 110 as input, volumetric input could also be generated from any other suitable source, including other imaging system sources such as ultrasound imaging systems, beta scan imaging, radionuclide scanning, thermography and the like. Anatomical volumetric input data could also be artificially fabricated from idealized versions of anatomical features, which may be initially obtained from CT-data and modified, or be created manually by modeling such idealized version. These could be created to test medical devices within anatomical features having specified characteristics. For example, it may be desirable to test a medical device in an aorta having two distended sections caused by aortic aneurysms, which are separated by a non-distended portion of the aorta. Input data representing such an anatomical feature could be generated by manually entering data known to wholly represent such an anatomical feature. Alternatively, input data representing such an anatomical feature could be constructed by manually entering data corresponding to portions of CT, MRI or other imaging created data of actual patient aortas.

The output of the Mesh Generator 130 is then received by the Stress/Strain/Deformation Analyzer 160. The Stress/Strain/Deformation Analyzer 160 also receives Materials Model data 170 and Load data 150 as input, which may also be outputs of the Mesh Generator 130. The output of the Stress/Strain/Deformation Analyzer 160 comprises the medical device performance data for evaluation, which may then be received by the Visualization tool 180 as input. The Visualization tool 180 in turn displays, through animation or visual representations, the predicted stresses, strains, and deformations on the candidate prosthesis "virtually in vivo."

In an embodiment of the invention, the Geometry Generator 120 is a custom-developed software tool or the MIMICS software from Materialise NV (with offices in Ann Arbor, Mich., USA); the Mesh Generator 130 is TRUEGRID® of XYZ Scientific Applications, Inc. (Livermore, Calif., USA); the Stress/Strain/Deformation Analyzer 160 is a modified version of NIKE3D or DYNA3D available from Lawrence Livermore National Laboratory (LLNL); and the Visualization tool 180 is the GRIZ visualization software, also developed by LLNL.

The unique combination of tools, data, and processing techniques as described herein in conjunction with the preferred embodiment provides a more accurate in vitro representation of anticipated in vivo forces exerted on medical devices and thereby reduces cost and time in the fabrication and testing of prototypes.

The various systems or components 120, 130, 160, 180, inputs (e.g., via files), and outputs (e.g., via files) of the present invention may be contained in one or in a plurality of computers. Thus, the Geometry Generator may be contained in one computer, while the Stress/Strain/Deformation Analyzer and the Visualization tool are run and contained in a separate computer. Furthermore, the inputs need not directly be received by the receiving system, e.g., through a network transmission. The outputs for example, of the Geometry Generator may be stored in a floppy disk and read by a Mesh Generator via that floppy disk.

Figure 2:
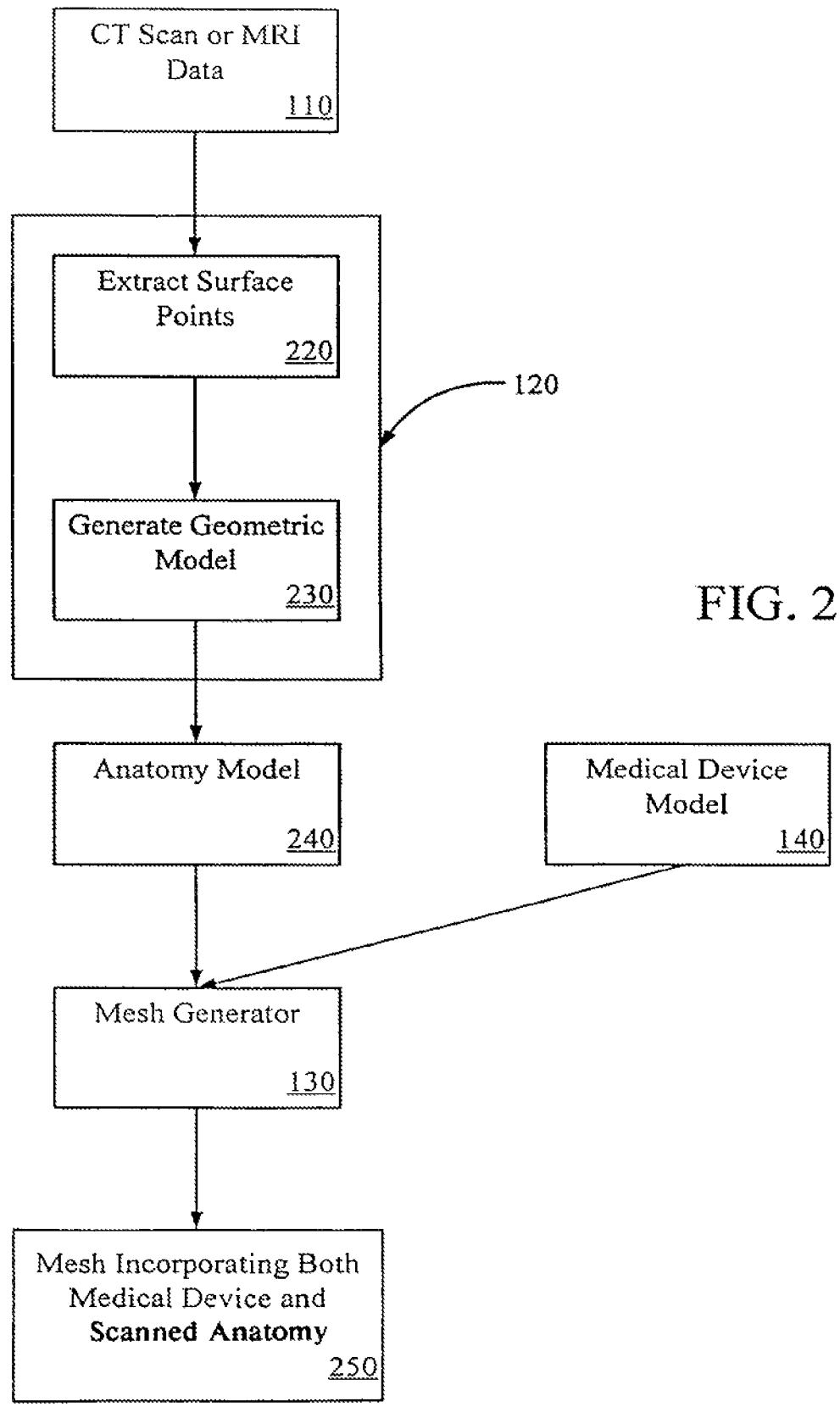
FIG. 2 illustrates a block diagram showing data received by an embodiment of a Geometry Generator and a Mesh Generator in accordance with the present invention.

FIG. 2 shows the data flow for an embodiment of a Geometry Generator 120 of FIG. 1 in detail. The Geometry Generator 120 receives as input the CT scan, MRI data, or other three-dimensional (3D) volumetric data 110. It is preferred that data from CT scans or MRIs be used in this invention because they provide a 3D volumetric representation of patient anatomy and blood vessel morphology, including complex atherosclerotic plaque distribution within the flow lumen. This type of data thus provides an accurate representation, for example, of the environment on which a medical device, for example, a TPEG will be placed. The CT and MRI equipment that is used to capture such 3D volumetric data are those that are readily available.

Certain researchers and scientists in the biological sciences have at their disposal a wealth of voxel data. A voxel is the unit of CT or MRI reconstructions, represented as a pixel in the display of the CT scan or MRI. Well-established methods to extract triangular surface representations (hereinafter referred to "surface points") from these voxel data using criteria such as variation in density are available. An embodiment of the Geometry Generator 120 first extracts the surface points, at step 220, from the CT scan or the MRI image data (e.g., segmentation, contour based, or 3D approach). A CAD software is then used to generate the Geometric Model 230 of the anatomy scanned using the extracted surface points. The extraction of surface points can be implemented by writing a software program that implements the techniques stated above or by available software programs. An example of a software program that generates surface points based on CT scan or MRI data is PREVIEW from Medical Media Systems.

The output of the Geometry Generator 120 is in the form of an Anatomy Model 240, which contains the geometric model of the anatomy scanned. The Anatomy Model 240 and the Medical Device Model 140 (containing the geometric model of the candidate medical device) are then received by the Mesh Generator 130 as input (usually as CAD files). The anatomy model may be a portion or an element of the anatomy scanned. Similarly, the medical device model may be a portion or of an element of the candidate medical device. This is useful for analyzing the interaction between a portion of a candidate device, such as a proximal stent in a TPEG, and a certain anatomical feature, such as tissue. The Mesh Generator 130 then generates a finite element model incorporating both the anatomy model, whether idealized or actual, and the medical device model as represented by box 250.

In one embodiment, the geometric models of the anatomy and the medical device are created using CAD software. Generally, the geometric models are stored in the Initial Graphics Exchange Specification (IGES) format that is an industry-standard graphic file format for CAD systems. Because of its wide-use, many FEA software tools read and utilize the IGES format. In another embodiment, the geometric models are created directly in the Mesh Generator.

The Mesh Generator 130 in accordance with an embodiment of the invention is TRUEGRID®. TRUEGRID is a 3-D finite modeling and analysis tool that generates meshes or finite element models. It is a software that tessellates a geometric model into hexahedron brick elements and quadrilateral shell elements, creating a mesh or a grid. A FEA mesh generating tool, such as TRUEGRID, uses the anatomy model 240 and medical device model 140 created by a CAD software to generate a mesh. In another embodiment of a Geometry Generator 120 (not shown in the figures), the Geometry Generator is a software tool that interfaces between scanner data, such as CT, MRI, and technical scanner data, and Rapid Prototyping, CAD, or Finite Element analysis data. Such software tools typically generate surface points from such scanner data, which are then converted into STL (stereolithography), slice files, and/or IGES files, which may then be read by the Mesh Generator 130 as input. An example of such a Geometry Generator 120 is the "Materialise Interactive Medical Image Control System" (MIMICS) available from Materialise, referred to above. The output of the MIMICS program, for example, may be directly read and processed by the Mesh Generator 130. Thus, steps 220 and 230, illustrated in FIG. 2, are not necessarily implemented by this alternative embodiment of the Geometry Generator 120.

Figure 3:
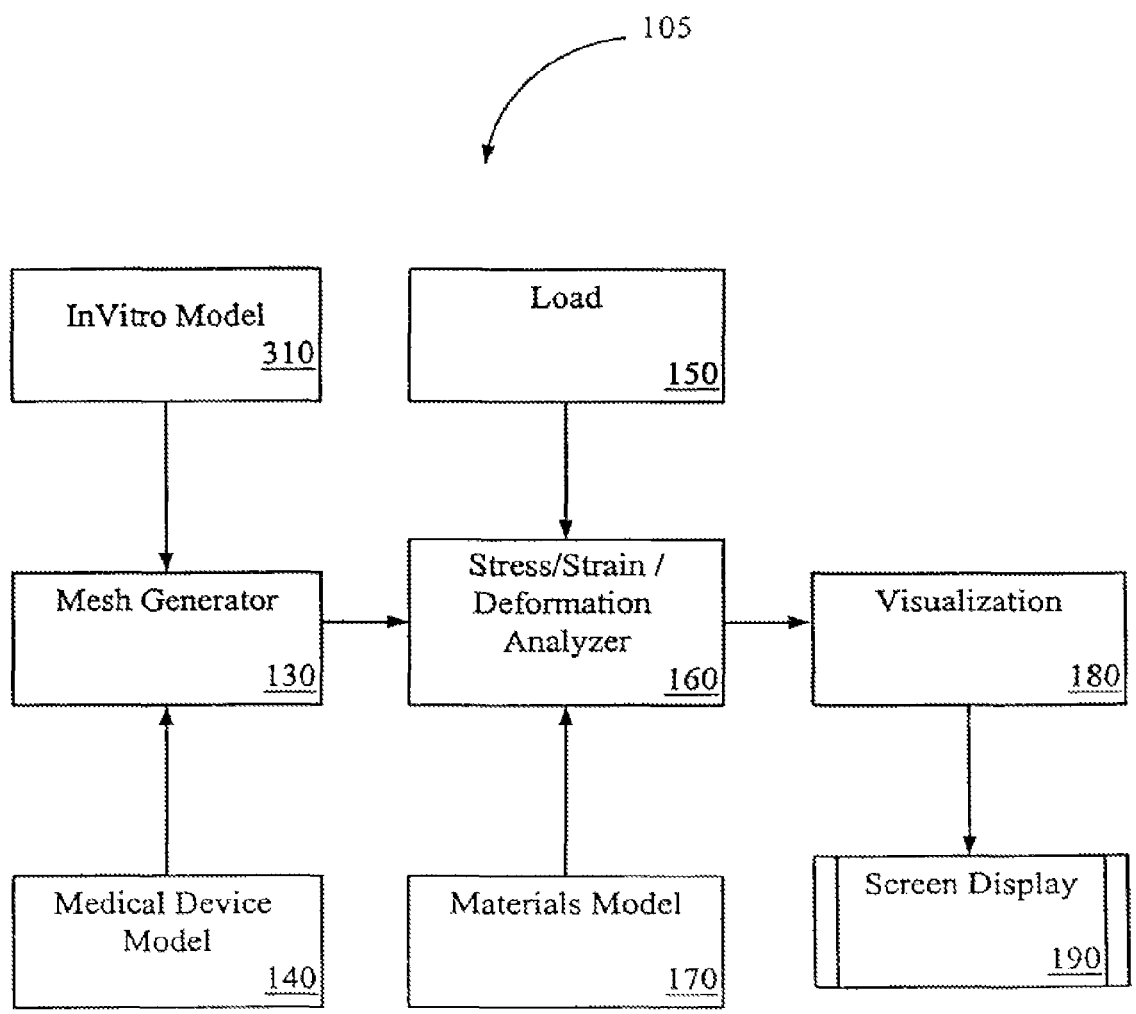
FIG. 3 illustrates a block diagram representation of another embodiment of a system of the present invention.

FIG. 3 is a block diagram showing another embodiment of a virtual prototyping system 105. FIG. 3 is similar to FIG. 1, except that the anatomical feature is not obtained from a 3D volumetric data, such as a CT scan. Rather, an in vitro model of the anatomical feature is presented for analysis. For example, instead of a CT-scan artery, the system analyzes the stresses, strains, and deformations of a medical device deployed in a latex tube, which represents the artery or the in vitro model. Such in vitro model may be a CAD file that is read by the Mesh Generator 130 or in another embodiment created within the Mesh Generator itself. Alternatively, an idealized anatomical feature may be created through this embodiment. In another embodiment of the invention, not shown in the figure, the system may do a component or element analysis of a proposed medical device, without the incorporation of either an anatomical feature or in vitro model.

Figure 4:
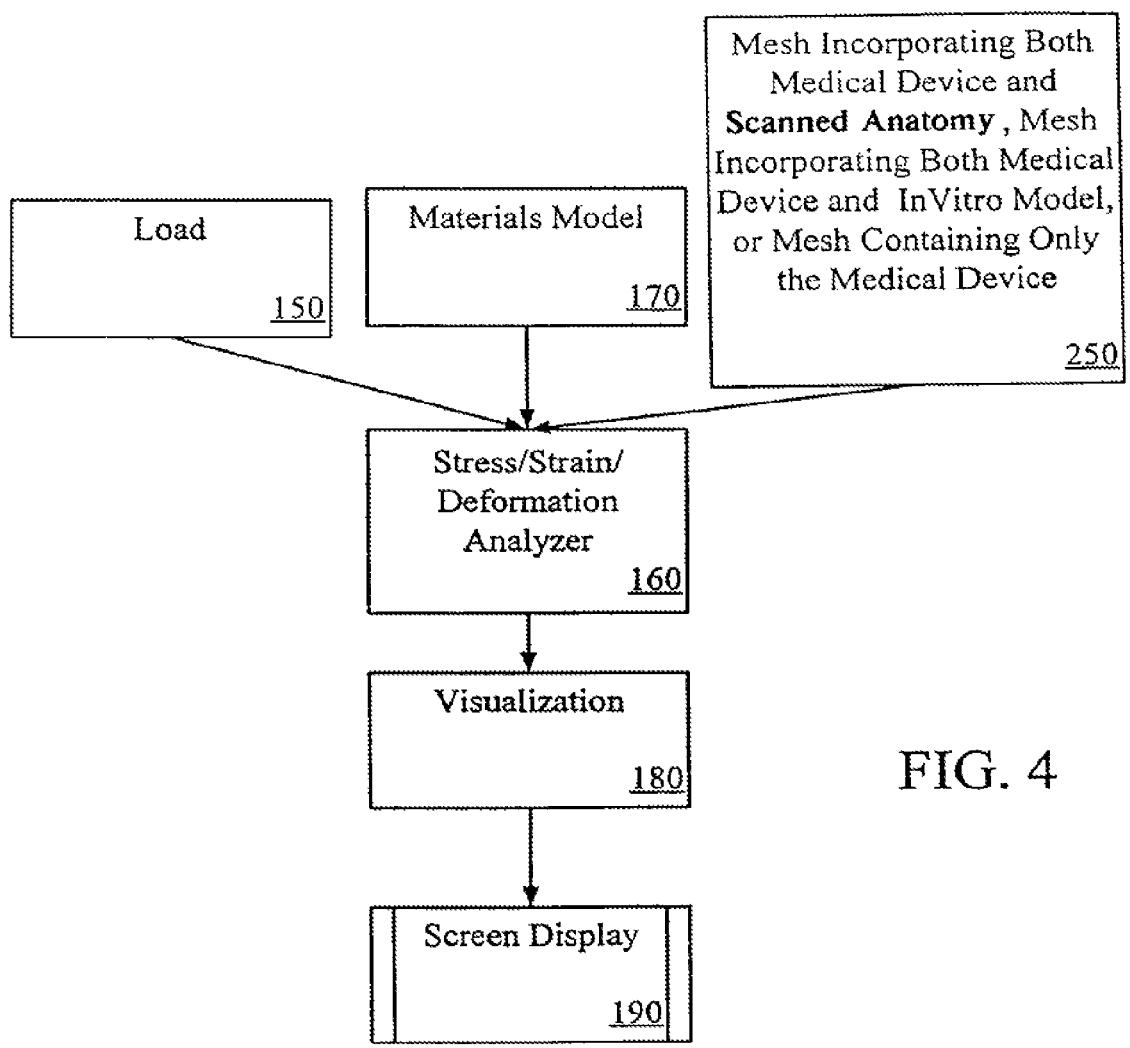
FIG. 4 illustrates a block diagram showing data received by a Stress/Strain/Deformation Analyzer.

FIG. 4 is a block diagram showing in detail the data flow of the Stress/Strain/Deformation Analyzer 160, which preferably is a non-linear finite element modeling software application such as DYNA3D or NIKE3D. The Stress/Strain/Deformation Analyzer receives a mesh incorporating both the medical device and the anatomy scanned (idealized or actual), a mesh incorporating both the medical device and in vitro model, or a mesh incorporating just the medical device model 250. A portion of the medical device, in vitro model, or the anatomy scanned may be used. The Stress/Strain/Deformation Analyzer 160 also receives the Materials Model 170, and the Load 150 on the applicable structures (e.g., TPEG and artery or just on the medical device) to generate an output used by the Visualization tool 180. In the preferred embodiment, the Materials Model 170 and the Load 150 are read by TRUEGRID through a command file (further discussed below). Thus, the outputs of TRUEGRID (the Mesh Generator) do not only include the finite element model 250 of the mesh incorporating both medical device and anatomy scanned, mesh incorporating both medical device and in vitro model, or a mesh containing only the medical device, but the materials model 170 parameters as well as load 150 information. This reduces the number of code changes, if necessary, within DYNA3D or NIKE3D, or the manual entry of input values to be read by DYNA3D or NIKE3D.

DYNA3D is a general-purpose, explicit, three dimensional, finite element program for analyzing and simulating the large deformation dynamic response of inelastic solids and structures. DYNA3D and NIKE3D implement a number of material models, for example, including elastic, orthotropic elastic, and kinematics/isotropic plasticity. NIKE3D is a general-purpose nonlinear implicit, three-dimensional, finite element program for analyzing and simulating the finite strain and static and dynamic response of inelastic solids, shells, and beams.

FEA Stress/Strain/Deformation Analyzers, such as DYNA3D and NIKE3D, are capable of analyzing and simulating sliding interfaces, body force loads due to base acceleration, body force loads due to spinning (geometry-dependent), concentrated nodal loads, pressure boundary conditions (geometry-dependent), and displacement boundary conditions.

The Materials Model 170 is the numerical representation of the material characteristics of the medical device, the anatomy, and/or the in vitro model being analyzed. Loads include pressures, displacement, forces, and deformations.

Using the mesh 250, the Materials Model 170, and the Load 150, the Stress/Strain/Deformation Analyzer 160 then analyzes and simulates the non-linear stress, strain, and deformation over time such as on a medical device (e.g., a TPEG and the arterial wall). The Stress/Strain/Deformation Analyzer in accordance with an embodiment of the present invention utilizes non-linear analysis (e.g., using non-linear formulas) or linear analysis to simulate and to analyze the non-linear static or dynamic behavior in the structure.

In FIG. 4, the Materials Model 170 is directly received by the Stress/Strain/Deformation Analyzer 160. Another way to have the materials model be received by the Stress/Strain/Deformation Analyzer 160 is by modifying the source code of DYNA3D and NIKE3D, e.g., by hard-coding the materials model into the source code itself. Similarly, if the source code of the geometry generator, Mesh Generator, Stress/Strain/Deformation Analyzer, and/or Visualization tool are available, inputs as shown may be incorporated, for example, by actually hard-coding the input parameters into the source code or by changing certain equations in the code itself.

Once the Stress/Strain/Deformation Analyzer 160 has analyzed the stresses, strains, and deformations on the medical device, the Visualization module 180 (in FIG. 1) can then receive the output of the Stress/Strain/Deformation Analyzer to visually display the resulting stresses, strains, and deformations 190.

Generally, the numerical output of the Stress/Strain/Deformation Analyzer 160 may also be analyzed to determine the stresses, strains, deformations on the medical device without using the Visualization tool 180. Using the Visualization tool 180, however, facilitates such determination because the stresses, strains, and deformations are shown via a graphical and visual display. A virtual prototyping or simulation of a medical device design, rather than plain numerical output data, is thus produced.

In an embodiment, the Visualization tool 180 is provided by the above-referenced GRIZ software application. GRIZ is an interactive software for visualizing FEA results on three-dimensional unstructured grids, and calculates and displays derived variables from FEA software tools such as DYNA3D, NIKE3D, and TOPAZ3D (also developed by LLNL). GRIZ provides display control of the mesh materials on an individual basis, allowing the user to concentrate on the analysis and visually focus on important subsets of the mesh, and provides the ability to animate the representation over time.

GRIZ uses the Silicon Graphic Inc. (SGI) Graphics Library (GL) or Open GL for rendering and the "Motif widget" toolkit for its user interface. In order to compile and run GRIZ, both of these libraries are required. GRIZ can be used on SGI workstations as well as on SUN and other workstations using commercial GL emulation software.

Considering the visual result on the screen display 190, a user may then compare the candidate medical device as designed against selected performance requirements. If the selected design meets the performance requirements, then a prototype of the selected medical device design may be built and tested. In addition, the visual result on the screen display 190 can be used by a physician to aid in the selection of various versions (e.g., sizes) of a given medical device design. For example, prior to a procedure for placement of a TPEG in a patient's aorta, the physician may first virtually test the performance of various TPEG designs or various versions of a single TPEG design prior to the procedure. To accomplish this, the physician would obtain volumetric data from the patient's aorta by any of the various methods discussed above and input that data into an embodiment of a system 105 (in FIG. 1) for analyzing the use of a medical device. The same or similar type of volumetric and materials data for a version of TPEG design to be tested is also loaded into the system 105. Note that it may be possible to load volumetric data from several anatomical features and versions of TPEG designs to be analyzed at one time, and then for the physician to choose which two to test together at a later time. Once the input data is loaded into the system 105, the visual result of the analysis of the Stress/Strain/Deformation Analyzer 160 is viewed by the physician on the screen display 190 and based on those results, the physician determines whether the TPEG version tested meets, exceeds, or falls short of the clinical requirements of the patient.

If the version of the TPEG which was virtually tested by the system 105 falls short of the clinical requirements of the patient, another version may be tested and so on until an appropriate design is identified. The physician may then begin the actual procedure on the patient with the appropriate TPEG design version. The system 105 may be configured to display the performance of a given TPEG design version with regard to long term structural integrity, prevention of perigraft leaks or sealing function, the general sizing of the TPEG with respect to the patient's aorta and the Like. With regard to testing of the long term durability or structural integrity of the TPEG or other medical device design, the system 105 has great utility. Specifically, system 105 has the ability, assuming the use of sufficiently powerful CPUs, to recreate large numbers of cyclic expansions and contractions in a short period of time. For example, as discussed above, the vascular system of a patient is constantly expanding and contracting as a result of dynamic or static pressure gradients within the vasculature from the patient's beating heart. These expansions and contractions can put stresses, strains, and deformations on intracorporeal medical devices, such as TPEG, which over time can lead to failure of the device. System 105 would give the physician the ability to quickly test a chosen TPEG design in a virtual model of the patient's expanding and contracting aorta for an amount of cycles that would equal or exceed the amount of cycles that would be expected in the patient's lifetime to determine the long term safety and efficacy of the design choice. Of course, a similar time compressed analysis could be used for any other type of medical device in any other part of a patient's body. Accordingly, if the invention is used as a preprocedure tool, physicians may analyze the use of various TPEG embodiments and select those that meet their performance requirements thereby allowing the physicians to select the best medical devices, such as the best TPEGs for treating their patients with aneurysm.

Because of the computing resources needed by FEA software tools, they are generally rim on Silicon Graphics or other UNIX computer systems. The Mesh Generator, Stress/Strain/Deformation Analyzer, and the visualization of the stresses, strains, and deformations on the candidate TPEG have been run on a Silicon Graphics (R12000) machine with 640 MB of memory.

Modifications to DYNA3D or NIKE3D

In one embodiment, NIKE3D and DYN/A3D were used and modified to implement the features of the present invention (TPEG design was analyzed). In determining the required material model, an exemplary material model (herein called TPEG material model (W)) was used to accommodate a strain energy density of the form:

$$W = a_{10}(I_1-3) + a_{01}(I_2-3) + a_{20}(I_1-3)^2 + a_{11}(I_1-3)(I_2-3) + a_{02}(I_2-3)^2 + a_{30}(I_1-3) + a_{21}(I_1-3)^2(I_2-3) + a_{12}(I_1-3)(I_2-3)^2 + a_{03}(I_2-3)^2 + \tfrac{1}{2}K(I_3-1)^2$$

with $K = 2(a_{10}+a_{01})/(1-2v)$ where
- $a_{ij}$ are material parameters;
- v is Poisson's ratio;
- K is the bulk modulus given as a function of Poisson's ratio; and
- $I_1, I_2, I_3$ and are the first, second, and third invariants of the right Cauchy-Green strain tensor, respectively.

The TPEG material model (W), discussed above, was derived from a doctoral thesis, which discusses the stress in abdominal aortic aneurysm. (See Madhavan Lakshmiraghavan, Mechanical Wall Stress in Abdominal Aortic Aneurysm: Towards Development of a Clinical Tool to Predict Aneurysm Rupture (1998) (unpublished Ph.D. dissertation, University of Pittsburgh which is hereby incorporated herein in its entirety).

Other articles discussing a hyperelastic material, linear elastic, and non-linear elastic models of the aortic walls may also be used to derive a material model as exemplified above and other applications of the virtual prototyping system 105 (in FIG. 1). (See M. L. Raghavan et al., *Ex Vivo Biomechanical Behavior of Abdominal Aortic Aneurysm: Assessment Using a New Mathematical Model*, 24 Annals of Biomedical Engineering 573-582 (1996); David A. Vorp. Et al., *Finite Element Analysis of the Effect of Diameter and Asymmetry on the Wall Stress Distribution in Abdominal Aortic Aneurysm*, 35 BED (Bioengineering Conference ASME 1997) 33-34 (1997), both of which are incorporated by reference herein in their entirety).

Modifications to NIKE3D

NIKE3D has an existing material model, number 15, which is a three-dimensional continuum hyperelastic material that uses a strain energy density function of the form:

$$W = A(I_1-3) + B(I_2-3) + 1/2K(\ln\theta)^2$$

with $$K = \frac{4(A+B)(1+v)}{(3-6v)}$$

where
- A and B are material parameters;
- v is Poisson's ratio;
- K is the bulk modulus given as a function of Poisson's ratio;
- $I_1$ and $I_2$ are the first and second invariants of the right Cauchy-Green strain tensor, respectively; and
- θ is the current volume of the element divided by the undeformed volume.

Using the material model 15 as the framework, the material model 15 is modified to implement the TPEG Material Model "W" listed above. This entails ensuring that variables are accordingly updated or modified in the source code to capture the information required by the TPEG Material Model. Material model 15 was chosen from the NIKE3D models because it involves the least amount of code modification to implement the features of the present invention.

Implementation of the TPEG Material Model in NIKE3D

To implement the features in accordance with the present invention, two NIKE3D subroutines, weval.f and printm.f, were modified.

The following modifications were made to NIKE3D subroutine weval.f:

a) Ten material parameters ($a_{10}, a_{01}, a_{20}, a_{11}, a_{02}, a_{30}, a_{21}, a_{12}, a_{03}$, K) were read instead of three (A, B, and K).

b) The calculation of K was changed from K=4(A+B)(1+v))/(3−6v) to K=2($a_{10}+a_{01}$)/(1−2v)

c) The calculation of $$\frac{\partial W}{\partial I_1}$$

was changed from $$\frac{\partial W}{\partial I_1} = A$$

to $$\frac{\partial W}{\partial I_1} = a_{10} + 2a_{20}(I_1-3) + a_{11}(I_2-3) + 3a_{30}(I_1-3)^2 + 2a_{21}(I_1-3)(I_2-3) + a_{12}(I_2-3)^2$$

d) The calculation of $$\frac{\partial W}{\partial I_2}$$

was changed from $$\frac{\partial W}{\partial I_2} = B$$

to $$\frac{\partial W}{\partial I_2} = a_{01} + a_{11}(I_1-3) + 2a_{02}(I_2-3) + a_{21}(I_1-3)^2 + 2a_{12}(I_1-3)(I_2-3) + 3a_{03}(I_2-3)^2$$

e) The higher derivatives of W with respect to $I_1$ and $I_2$ were changed from zero to $$\frac{\partial^2 W}{\partial I_1^2} = 2a_{20} + 6a_{30}(I_1-3) + 2a_{21}(I_2-3),$$

$$\frac{\partial^2 W}{\partial I_2^2} = 2a_{02} + 2a_{12}(I_1-3) + 6a_{03}(I_2-3), \text{ and}$$

$$\frac{\partial^2 W}{\partial I_1 \partial I_2} = a_{11} + 2a_{21}(I_1-3) + 2a_{12}(I_2-3)$$

f) The derivatives with respect to $I_3$ were changed from $$\frac{\partial W}{\partial I_3} = K(\ln I_3 / I_3)$$

to $$\frac{\partial W}{\partial I_3} = K(I_3-1) \text{ and from } \frac{\partial^2 W}{\partial I_3^2} = K((1-\ln I_3)/I_3^2) \text{ to } \frac{\partial^2 W}{\partial I_3^2} = K$$

g) When a completely incompressible material ($I_3=1$) is specified by setting the augmented Lagrangian flag to true, the derivatives with respect to $I_3$ are left in the log form. The log form shows substantially faster convergence and better stability for completely incompressible materials.

The NIKE3D subroutine printm.f was modified to print out all nine a material parameters to the material description in the high-speed printout file.

Invocation of the Modified NIKE3D TPEG Material Model

The TPEG material model (W) (i.e., the modified NIKE3D Material Model 15) is invoked in NIKE3D using the input data format shown in Table I. Poisson's ratio is kept as the third parameter to maintain compatibility with models using the original NIKE3D hyperelastic model. The documentation for NIKE3D, and the TRUEGRID Mesh Generator, provides an input format list for Material Model 15 similar to Table I given below, with A, B, and v all defined on card 3 (it should be understood that the "card" represents lines of input data). The original NIKE3D code, however, reads A from columns 1-10 card 3, B from columns 1-10 of card 4, and v from columns 1-10 of card 5. This format was changed to comply with the NIKE3D manual and the format in Table I in the modified weval.f and printm.f subroutines.

TABLE I

Input parameters format for the modified NIKE3D material model (TPEG material model)

| Card | Columns | Description | Format |
|---|---|---|---|
| 1 | 1-5 | Material ID number | I5 |
| 1 | 6-10 | Material type (use 15) | I5 |
| 1 | 11-20 | Density | E 10.0 |
| 1 | 21-25 | Element class (not used) | I5 |
| 1 | 26-35 | Reference temperature (not used) | E 10.0 |
| 1 | 36-45 | Rayleigh damping parameter alpha | E 10.0 |
| 1 | 46-55 | Rayleigh damping parameter beta | E 10.0 |
| 2 | 1-72 | Material title | 12A6 |
| 3 | 1-10 | $a_{10}$ | E 10.0 |
| 3 | 11-20 | $a_{01}$ | E 10.0 |
| 3 | 21-30 | Poisson's ratio | E 10.0 |
| 3 | 31-40 | $a_{20}$ | E 10.0 |
| 3 | 41-50 | $a_{11}$ | E 10.0 |
| 3 | 51-60 | $a_{02}$ | E 10.0 |
| 3 | 61-70 | $a_{30}$ | E 10.0 |
| 3 | 71-80 | $a_{21}$ | E 10.0 |
| 4 | 1-10 | $a_{12}$ | E 10.0 |
| 4 | 11-20 | $a_{03}$ | E 10.0 |
| 5-7 | All | Blank | |
| 8 | 1-10 | Augmented Lagrangian flag .EQ.1: active, enforce compressibility with augmented Lagrangian iteration | E 10.0 |
| 8 | 11-20 | Convergence tolerance for augmented Lagrangian iteration .GT.0.0: converged when volume strain norm < TOL (tolerance) .LT.0.0: augment exactly-TOL times | E 10.0 |

The format column specifies the expected data type. For example, a format of "1" means that an integer is expected ("IS" means integer with 5 positions), "E" means a real numeric value, and "A" means character data type.

Modifications to DYNA3D

DYNA3D has an existing material model number 27, which is a three-dimensional continuum hyperelastic material that uses a strain energy density function of the form $$W = A(I_1-3) + B(I_2-3) + C(I_3^2-3) + D(I_3-3)^2$$

with $C = \frac{1}{2}A + B$ and $$D = \frac{A(5v-2) + B(11v-5)}{2-4v}$$

where:
A and B are material parameters;
v is Poisson's ratio; and
$I_1$, $I_2$, and $I_3$ are the first, second, and third invariants of the right Cauchy-Green strain tensor, respectively.

The material model 27 may be modified to implement the TPEG Material Model (W)). This also entails ensuring that variables are accordingly updated or modified in the source code to capture the information for the TPEG material model (W).

Implementation of the TPEG Material Model in DYNA3D

To implement the features in accordance with the present invention, two DYNA3D subroutines, f3dm27.f and printm.f, were modified. The "$C(I_3^{-2}-1)$" term was left in the modified material model since without it, the explicit time integrator becomes unstable very easily. This term only significantly changes the result when the material undergoes significant change in volume. If v≈0.5, the material behaves in a nearly incompressible matter, in this case D is much larger than C, and the inclusion of C has little to no effect on the final result.

The following modifications were made to DYNA3D subroutine f3dm27.f:

a) Ten material parameters ($a_{10}$, $a_{01}$, $a_{20}$, $a_{11}$, $a_{02}$, $a_{30}$, $a_{21}$, $a_{12}$, $a_{03}$, K) were read instead of four (A, B, C, and D).
b) The calculation of D was changed from D=(A(5v-2)+B(11v-5))/(2-4v) to D=($a_{10}+a_{01}$)/(1-2v)
c) The computation for $I_1$ and $I_2$ were added.
d) The calculation of $$\frac{\partial W}{\partial I_1}$$

was changed from $$\frac{\partial W}{\partial I_1} = A$$

to $$\frac{\partial W}{\partial I_1} = a_{10} + 2a_{20}(I_1-3) + a_{11}(I_2-3) + 3a_{30}(I_1-3)^2 + 2a_{21}(I_1-3)(I_2-3) + a_{12}(I_2-3)^2.$$

e) The calculation of $$\frac{\partial W}{\partial I_2}$$

was changed from $$\frac{\partial W}{\partial I_2} = B$$

to $$\frac{\partial W}{\partial I_2} = a_{01} + a_{11}(I_1-3) + 2a_{02}(I_2-3) + a_{21}(I_1-3)^2 + 2a_{12}(I_1-3)(I_2-3) + 3a_{03}(I_2-3)^2.$$

f) The calculation of $$\frac{\partial W}{\partial I_3} = 2D(I_3 - 1) - 2C(I_3^{-3} - 1)$$

remains unchanged, however, the value of D has changed.

The DYNA3D subroutine printm.f was modified to correctly output the hyperelastic material constants to the resulting high-speed printout file.

Invocation of the Modified DYNA3D Material Model (TPEG Material Model)

The TPEG material model (i.e., the modified DYNA3D material model 27) is invoked in DYNA3D using the input data format shown in Table H. Poisson's ratio is kept as the third parameter to maintain compatibility with models using the original DYNA3D hyperelastic model.

TABLE II

Input parameters format for the modified DYNA3D material model (TPEG material model)

| Card | Columns | Description | Format |
| --- | --- | --- | --- |
| 1 | 1-5 | Material ID number | I5 |
| 1 | 6-10 | Material type (use 15) | I5 |
| 1 | 11-20 | Density | E 10.0 |
| 1 | 21-25 | Element class (not used) | I5 |
| 1 | 26-35 | Reference temperature (not used) | E 10.0 |
| 1 | 36-45 | Rayleigh damping parameter alpha | E 10.0 |
| 1 | 46-55 | Rayleigh damping parameter beta | E 10.0 |
| 2 | 1-72 | Material title | 12A6 |
| 3 | 1-10 | $a_{10}$ | E 10.0 |
| 3 | 11-20 | $a_{01}$ | E 10.0 |
| 3 | 21-30 | Poisson's ratio | E 10.0 |
| 3 | 31-40 | $a_{20}$ | E 10.0 |
| 3 | 41-50 | $a_{11}$ | E 10.0 |
| 3 | 51-60 | $a_{02}$ | E 10.0 |
| 3 | 61-70 | $a_{30}$ | E 10.0 |
| 3 | 71-80 | $a_{21}$ | E 10.0 |
| 4 | 1-10 | $a_{12}$ | E 10.0 |
| 4 | 11-20 | $a_{03}$ | E 10.0 |
| 5-7 | All | Blank | |

Reading the doctoral thesis mentioned above, the appropriate values of input parameters may accordingly be provided as input to the Stress/Strain/Deformation Analyzer (see Madhavan Lakshmiraghavan, Mechanical Wall Stress in Abdominal Aortic Aneurysm: Towards Development of a Clinical Tool to Predict Aneurysm Rupture (1998) (unpublished Ph.D. dissertation, University of Pittsburgh).

TRUEGRID Command File

FIGS. 5A through 5M contain a command file that is an exemplary file read by TRUEGRID to implement the features of the present invention (e.g., for stent design). This exemplary command file illustrates a component-level analysis of a stent, without the option for simulating deployment into CT-based anatomy (isim mod=6, not present in the command file).

TRUEGRID, in its basic form, is not only a Mesh Generator, but is also a format generator. It outputs data in a certain format, which are then read by NIKE3D and/or DYNA3D. The invention utilizes both TRUEGRID's capability as a Mesh Generator and an output generator to create an output file (e.g., Tables I and II discussed above), containing the appropriate values that would be read by NIKE3D and DYNA3D, respectively. The outputs created by TRUEGRID may be created by other means, e.g., by other Mesh Generator software or proprietary software.

The command file (contained in FIGS. 5A-5M) contains the parameters and the instructions that are read by TRUE-GRID to generate the mesh and the output file(s), which are read by DYNA3D and/or NIKE3D.

The line numbers at the start of each line are only added to facilitate reference to particular lines in the command file and are not part of the command file. Text after the "c" are ignored by TRUEGRID (comments). To take advantage of the capabilities of TRUEGRID, the command file contains various parameters that help developers customize their simulation and/or Stress/Strain/Deformation analysis. Mesh generating tools, such as TRUEGRID, in the non-interactive mode, generally require that command files or similar files be created to enable them to generate finite element models. In the interactive mode, a finite element model may be created by a medical device designer (e.g., TPEG designer) using the options available in the interactive mode of TRUEGRID.

Referring to FIG. 5A, the inike parameter (lines 5 and 21) tells TRUEGRID that the output file is to be read by a NIKE3D Stress/Strain/Deformation Analyzer. The command file also tells TRUEGRID that the stent to be modeled is a full 3-segment stent design (line 6 and 22), the model is a full 360 degree model of a stent (lines 6 and 23), to model the stress on the initial expansion of the stent in vivo (lines 16 and 24), and to refine the elements by 2 in each direction of the cross section (lines 18 and 25). (Crowns can be a pointed or barbed portion of a stent—see lines 7 through 9). The command file thus enables TRUEGRID to generate a mesh and a model of a stent subjected to various component-level in vitro tests such as radial force and predelivery compression. Simulation of these tests enables a designer to refine and optimize the stent design for its intended application (e.g. as component of a TPEG or for treating occlusive disease).

TRUEGRID can also act like an interpreter. It reads the information contained in the command file, and interprets and processes the lines accordingly. For example, the text after the word "para" or "parameter" are parameters read by TRUE-GRID. These terms indicate the value or the formula that should be used by TRUEGRID. For example, line 21 denotes that the parameter Mike contains the initial value 1.

Line 46 in FIG. 5B means that the value of the parameter dCIA3 contains the value 0.0.

Line 138 in FIG. 5D indicates that the initial value of the parameter rocompcyl is the value evaluated by the formula "[0.95*(min(% RCyl3,% RCyl6,% RCyl12__1,% RCyl12__2)-% RW6)." TRUEGRID understands that the min function has to be evaluated. The min function compares the value contained in each variable, in this case, contained in RCyl3 (e.g., contains 1), RCyl6 (contains 0.005), RCyl12__1 (contains 0.987), and RCyl12__2(contains 0.0002), and returns the content of the variable, which holds the least value—0.0002 (value contained in Rcyl12__2). Assuming the variable RW6 contains the value 0.18, TRUEGRID then evaluates the rocompcly variable to contain 0.95*0.0002–0.18, which equals to negative 0.17981. This value is thus the initial value of rocompcyl when initially processed and read by TRUEGRID.

Embodiments of the invention can simulate various phases of TPEG use. For example, it calculates the stresses, strains, and deformations on the TPEG when it is compressed then decompressed for deployment, when the TPEG is compressed into the catheter for deployment, when the TPEG expands, and the like.

Referring to line 432, in FIG. 5L, the term "include" indicates to TRUEGRID that when the condition as defined in line 431 is met, the istent.mts_nike_solid file is read. The contents of this include file could be added in the command file itself.

For flexibility and readability, however, they were placed in a separate file. Programmers typically use include files, such as done in C or C++, for code control and ease of maintenance FIGS. 6A-6F contain an exemplary text of a command file called "seal.run" (line 2) read by TRUEGRID for a simulated TPEG graft deployment in a proximal aortic neck to generate a mesh incorporating both an anatomical feature and medical device and to output files that are read by a Stress/Strain/Deformation Analyzer.

FIGS. 7A-7C is an exemplary include file, called "tpeg.part_ct_aorta3," used by "seal.run" command file listed in FIGS. 6A-6F. See line 217 of FIG. 6F. This file contains the commands which read in surfaces created by the Geometry Generator 120 from CT data for the aorta and builds the mesh for the vessel.

FIGS. 8A-8L is another exemplary command file read by TRUEGRID used in the virtual prototyping system of the present invention for simulating stent deployment into an anatomy from CT-data, as opposed to a stent graft. The stent could be a part of a stent graft, could be intended for use to treat occlusive disease in the vasculature, or could even be used for nonvascular application, such as an esophageal stent.

The files listed in FIGS. 5A-5M, 6A-6F, 7A-7C, and 8A-8L are written to be read by TRUEGRID. Variations on such files are expected depending on the Mesh Generator 130 deployed in the system.

Figure 9A:
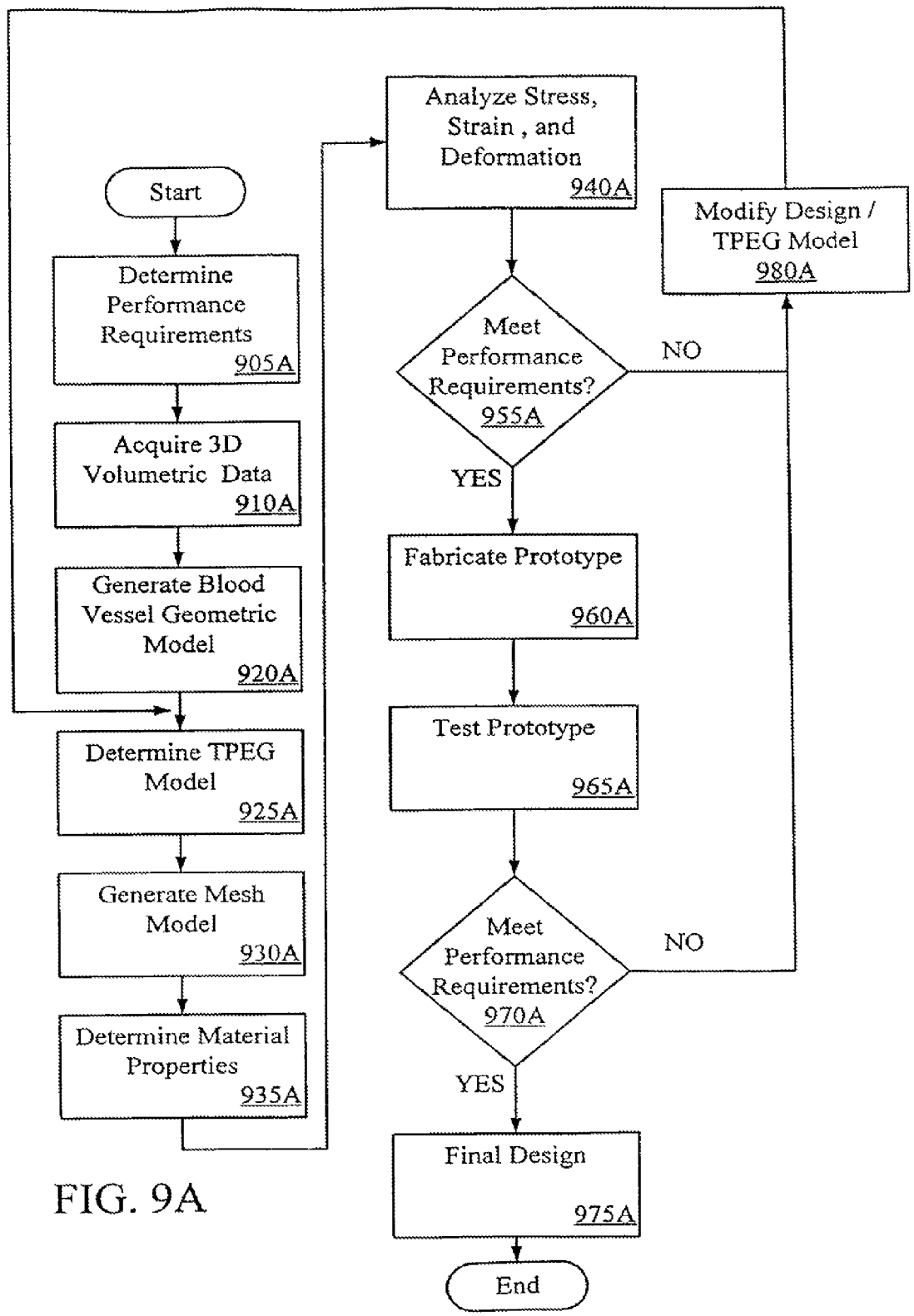
FIGS. 9A and 9B illustrate a process to develop better-designed medical devices, particularly TPEGs, in accordance with an embodiment of the present invention using 3D volumetric data.

FIG. 9A illustrates a flow chart, which sets forth the basic components of an embodiment of the inventive system and process in accordance with the present invention. In particular, this figure illustrates how to develop better-designed TPEGs. The steps illustrated may of course be utilized for developing other medical devices, other than TPEGs.

To start, a TPEG designer first determines, in box 905A, the performance requirements desired, such as to secure an optimal structural integrity of the TPEG, to avoid potential health risks such as ruptures and endoleaks, or to have a smaller TPEG packaging. 3D volumetric data of the anatomy desired, for example, in this case a blood vessel, is then acquired at box 910A, using CT or MRI scanners. Alternatively, if 3D volumetric data are already available, such acquisition may be skipped and such 3D volumetric data be obtained from the archive.

It should be noted here that the "anatomy" desired, which defines the embodiment in which a medical device is to be tested, is not necessarily limited to a patient's body. For example, embodiments of the present invention could be used to obtain test results for medical device performance in a wide variety of in vitro tests, some of which may be necessary or desirable for Food and Drug Administration (FDA) approval of the medical device in question. Various forms of in vitro failure mode testing such on tensile pull testing and the like could be performed by an embodiment of the invention and allow the tester to easily vary test parameters, device design, and test frequency to quickly obtain the desired test results. In addition, volumetric anatomical data for animals could be used to simulate animal testing that is necessary or desirable for FDA approval of a medical device. This may be of particular importance for a medical device design, which seeks to establish equivalence with an existing approved product which has been previously tested in animal studies.

The geometry generator (120 in FIG. 1) then generates a blood vessel geometric model in box 920A. As discussed above, the blood vessel geometric model may be an actual idealized or in vitro model. If the geometry generator is an embodiment where surface points are first extracted, a CAD system may then be used to generate such geometric model.

Next, a candidate TPEG model or design, which is obtained typically from a model created using a CAD software, is selected or modeled by the TPEG designer (step 925A). The Mesh Generator (130 in FIG. 1) then generates a mesh model incorporating both the blood vessel and the TPEG (930A). A TPEG designer then determines the material properties of the candidate TPEG model and the blood vessel at step 935A. The material properties may also have been assigned by the TPEG designer during the previous step (i.e., the generation of the mesh model). Using a Stress/Strain/Deformation Analyzer (160 in FIG. 1), assuming that the load (150 in FIG. 1) and the Materials Model (170 in FIG. 1) are available to the Stress/Strain/Deformation Analyzer for input, a TPEG designer then simulates the candidate TPEG design behavior in a stress/strain/deformation analysis (at step 940A) to determine if the candidate TPEG meets the performance requirements.

If the candidate TPEG does not meet the performance requirements, a "no" outcome at decision box 955A, the TPEG designer chooses another TPEG design or model at step 980A, and repeats the steps as shown by the arrow to box 925A. If it, however, meets the target performance requirements, a "yes" outcome at decision box 955A, a prototype is then fabricated based on the candidate TPEG model and design at step 960A. The fabricated prototype is then subjected to testing, e.g., animal testing or clinical testing, at step 965A. If the fabricated prototype meets the target performance requirements, the candidate TPEG model thus is a final design and may be used to produce other TPEGs.

If the fabricated prototype, however, does not meet the performance requirements, a "no" outcome at decision box 970A, the TPEG designer modifies the TPEG design or selects a new TPEG design, and repeats the steps as shown with the arrow to box 925A. If necessary, the process is repeated several times until the performance requirements and the final design is obtained. A benefit of the invention is to reduce the number of "no" outcome at decision box 970A compared to a development process which uses only hardware prototypes for design verification.

Figure 9B:
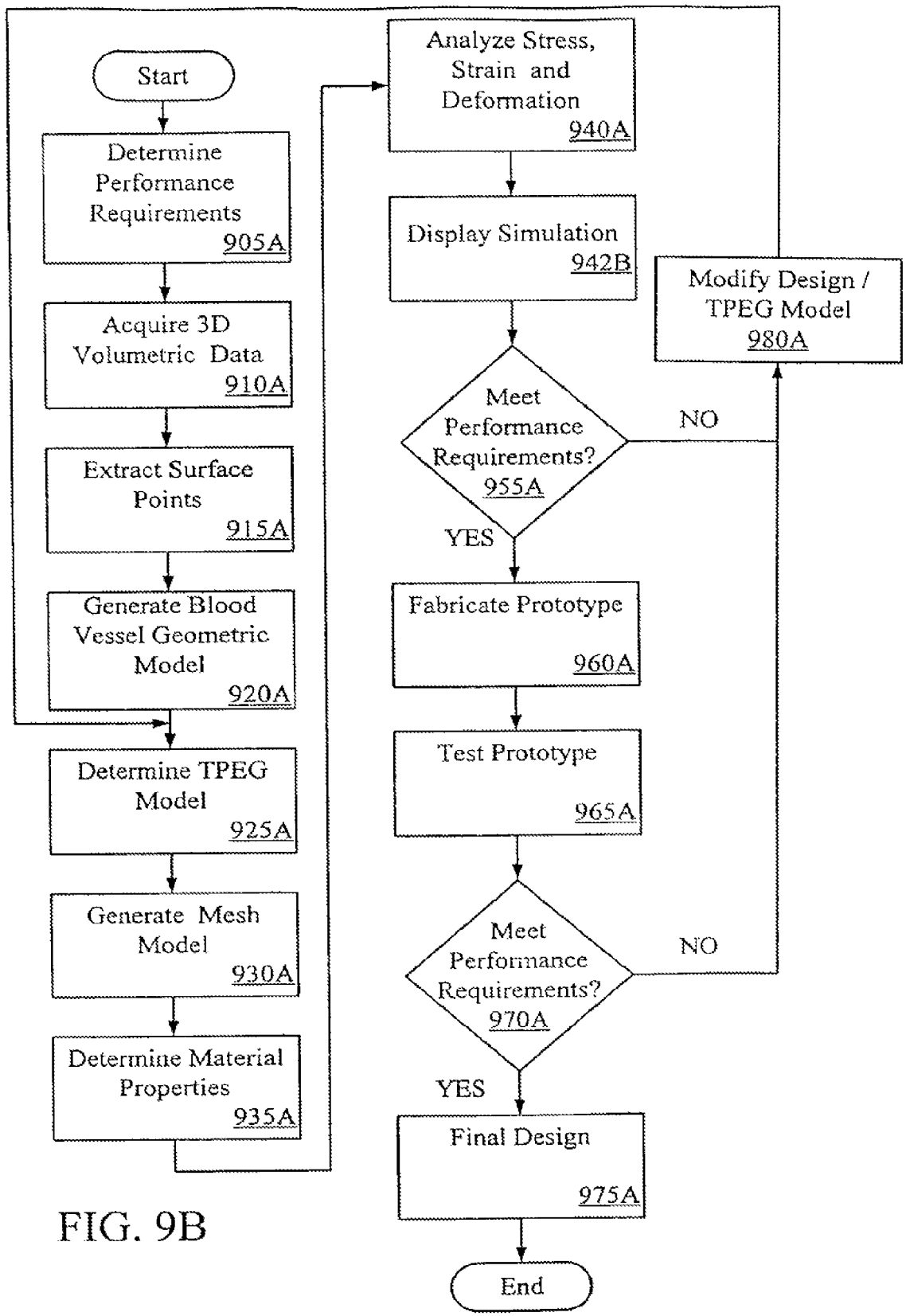

As discussed above, a proposed TPEG model may be evaluated against a number of anatomical features to determine the suitable range of conditions of an applicable TPEG model (e.g., size). Similarly, a set of anatomical features may be evaluated against a number of TPEG models to determine the type of suitable TPEG model for such set of anatomical feature. Furthermore, an analysis of the stresses, strains, and deformations may be conducted on the medical device without interaction to certain anatomical features. FIG. 9B, is similar to FIG. 9A except for the additional step (box 942B) of displaying the visual simulation of the stresses and strains on the TPEG. The display of the simulation is typically employed using the Visualization tool (180 in FIG. 1), which in the preferred embodiment is the GRIZ software.

Visual display of the simulation is not necessary because a reading of the numerical representation of the stresses, strains, and deformation on the TPEG may guide a TPEG designer whether the performance requirements are met. However, visual display is often desirable because a visual representation of the stresses and strains, for example, red hot spots on the visual TPEG model can be easier to understand than mere numerical representations.

Figure 10:
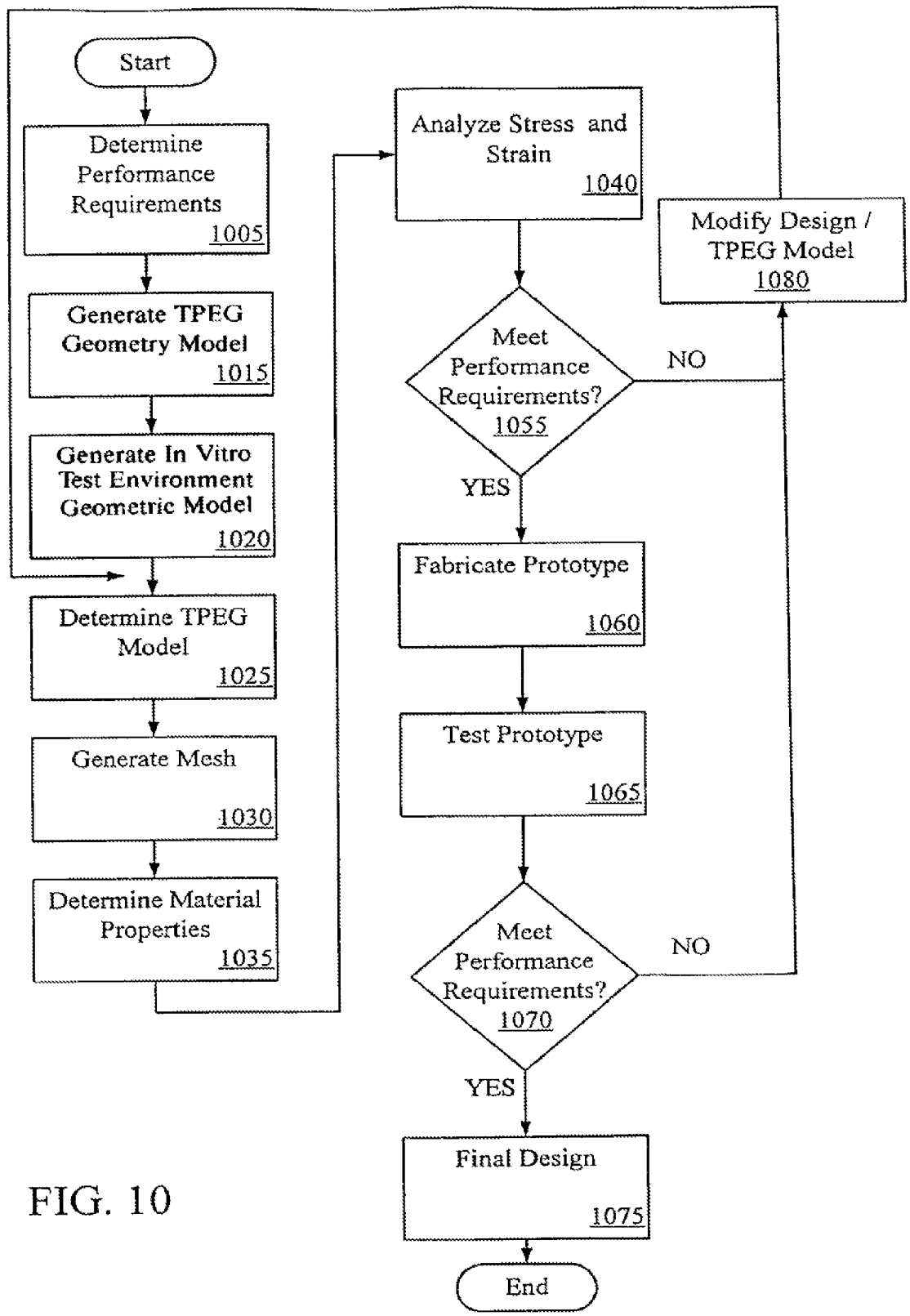
FIG. 10 illustrates a process to develop better-designed medical devices using in vitro anatomical features.

FIG. 10 is similar to FIG. 9A and illustrates a process to develop better-designed medical devices using in vitro features. In the first step as shown in 1005, a medical device designer, determines the performance requirements. The next step is to generate a geometry model of the in vitro model, step 1020A, (e.g., latex tube to represent an artery), using software tools, such as a CAD software or even TRUEGRID. The steps are then similar to those illustrated in FIG. 9A. In another embodiment, the in vitro model such as a latex tube may be scanned to obtain a 3D volumetric data. Such acquired 3D volumetric data may also be modified by the medical device designer.

In another embodiment not shown, only the medical device model is analyzed absent the anatomical feature or in vitro model. The operations shown in FIG. 10 would be implemented, without the operation of generating blood vessel geometric model (step 1020A) and the analysis would only be performed on the geometric model of the candidate medical device or a portion of it. Material properties and load information pertinent only to the medical device are generally used in the analysis process.

Figure 11:
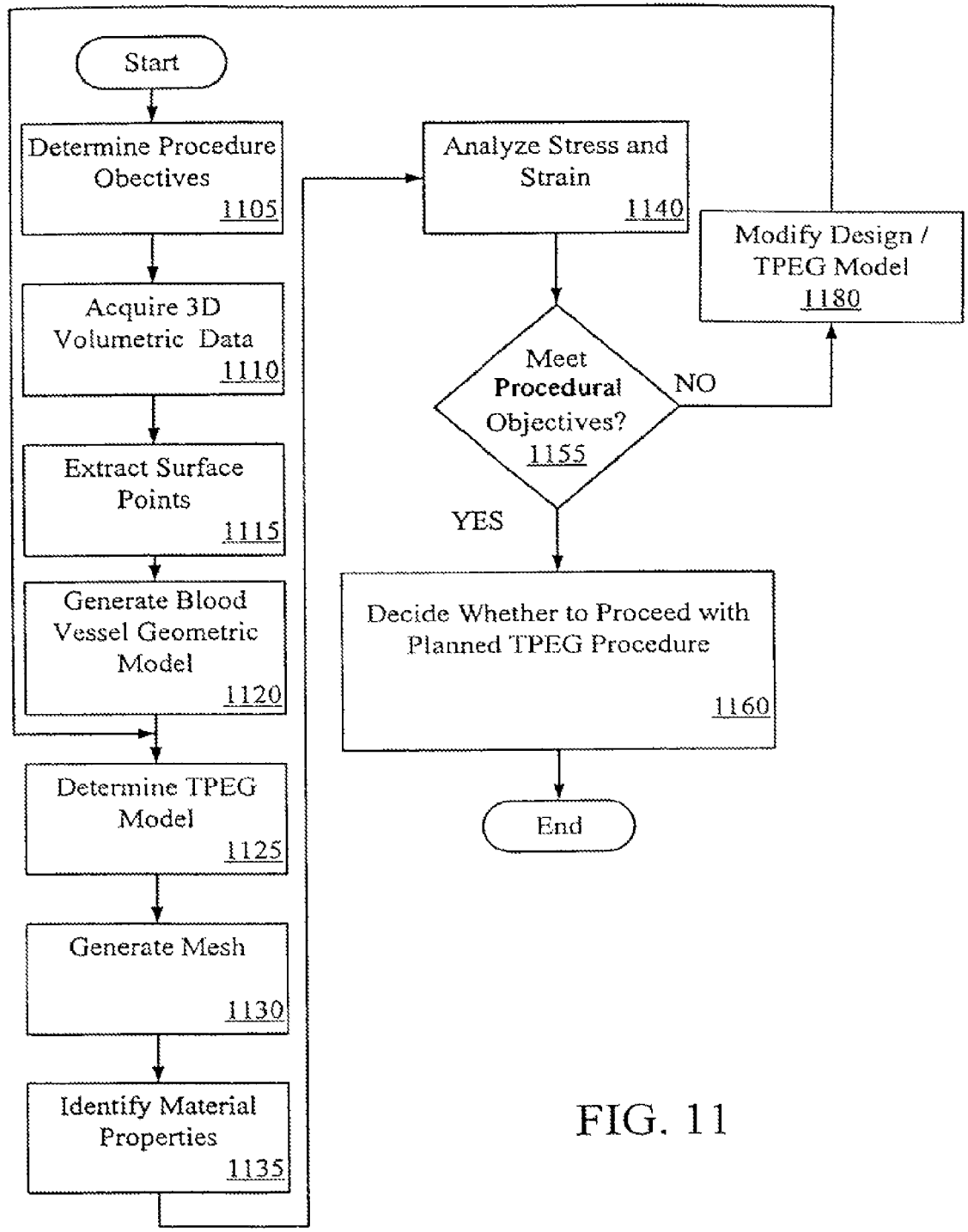
FIG. 11 illustrates the use of an embodiment of the present invention as a physician preprocedure planning tool.

FIG. 11 contains steps similar to those illustrated in FIG. 9A. FIG. 11 illustrates an embodiment of the present invention as a preprocedure planning tool, for example, to guide a physician in deciding which particular TPEG to implant in a patient.

To start, a physician first determines, in box 1105, the surgical or interventional procedure objectives, typically, to ensure robust sealing and structural integrity of the TPEG in vivo for a particular patient. The physician then obtains 3D volumetric data of the potential site of the TPEG, e.g., the abdominal aorta, at step 1110. The Geometry Generator (120 in FIG. 1) then extracts the surface points from the 3D volumetric data acquired in step 1115. Based on the surface points extracted, a blood vessel geometric model is created 1120.

Next, a candidate TPEG, which is obtained typically from a model created using a CAD software, is selected by the physician (step 1125). (TPEG models may be created in advance and stored in a library in the system. At this point, the physician is determining which available TPEG design is best suited for that patient or individual). The Mesh Generator (130 in FIG. 1) then generates a mesh model incorporating both the blood vessel and the selected TPEG. A physician may then identify the material properties of the candidate TPEG and the blood vessel at step 1135. The material properties may have also been assigned during the previous step (i.e., the generation of the mesh model). Using a Stress/Strain/Deformation Analyzer (160 in FIG. 1), assuming that the load (150 in FIG. 1) and the materials model (170 in FIG. 1) are available to the Stress/Strain/Deformation Analyzer for input, a physician may then run the candidate TPEG to a stress/strain/deformation analysis (at step 640) to determine if the candidate TPEG meets the surgical objectives.

If the candidate TPEG does not meet the procedural objectives, a "no" outcome at decision box 1155, a physician may decide to change the TPEG to be used in the procedure at step 1180 and repeat the process as shown by the arrow to box 1125. Based on the physician's judgment, if the candidate TPEG does meet the procedural objectives, a "yes" outcome at decision box 655, the physician then may decide whether to proceed with the planned TPEG implant procedure or not, at step 1160.

Figure 12:
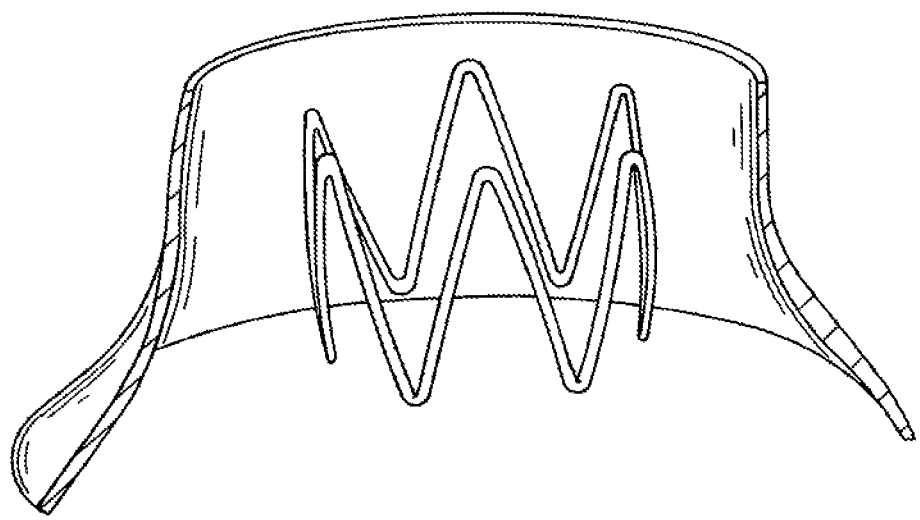
FIG. 12 contains a representation of one simulation display of a cutaway lateral view of a vascular stent in the infrarenal aorta just proximal to an abdominal aneurysm.
Figure 13:
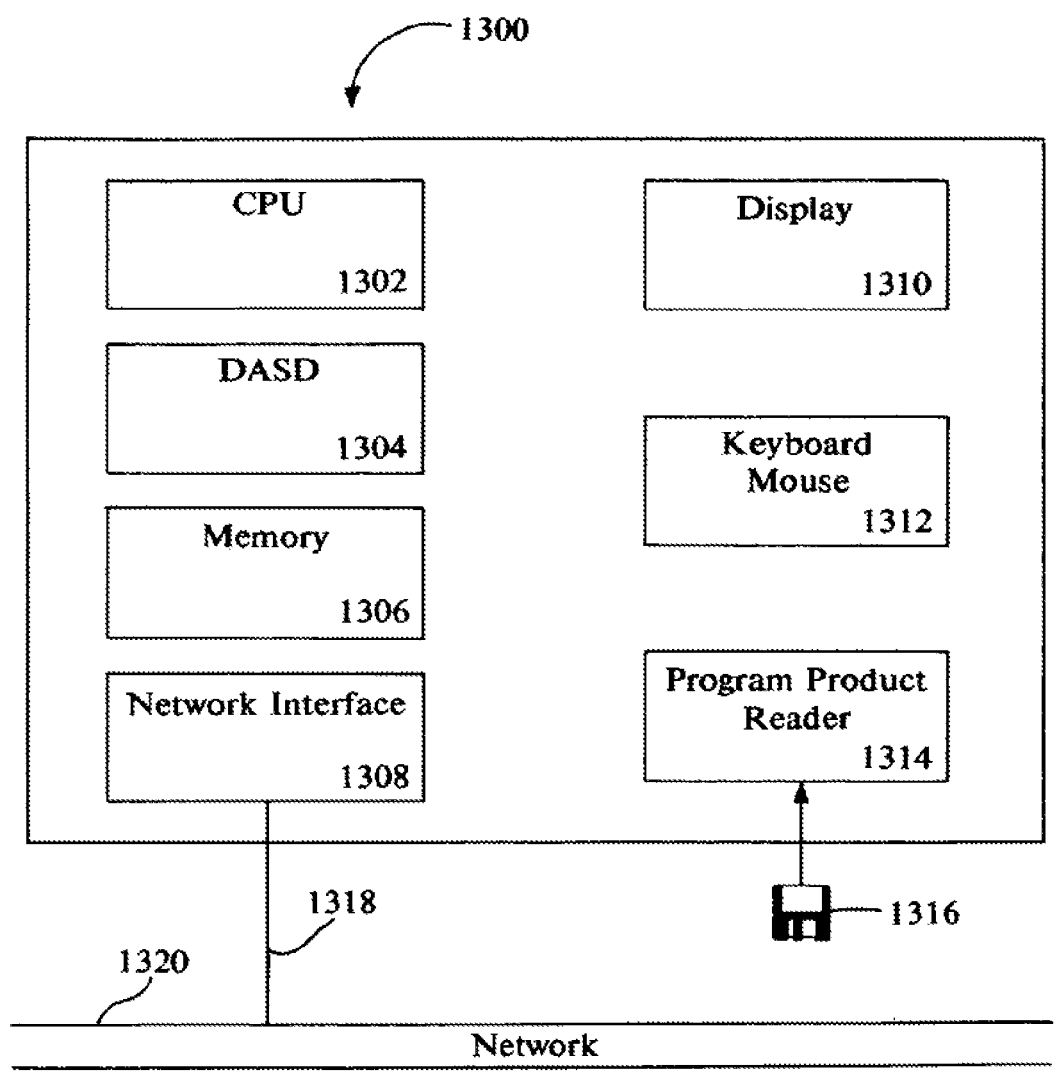
FIG. 13 is a block diagram representation of one of the computers illustrated in FIG. 1.

FIG. 12 contains a representation of one simulation display of a cutaway lateral view of a vascular stent in the infrarenal aorta just proximal to an abdominal aneurysm. Using the system as described above, several displays may be presented to the user showing the progressive stent expansion and contact with the luminal surface of the vessel. The system may be also be used such that the visualization module displays the medical device and the anatomical feature in color, with colors and their gradients representing the various stresses, strains, and deformations on the medical device and the anatomical feature. Other views, such as a proximal view, may also be used in simulation. FIG. 13 is a block diagram of an exemplary computer 1300 such as might comprise any of the computers containing a Geometry Generator 120, a Mesh Generator 130, a Stress/Strain/Deformation Analyzer 160, and a Visualization tool 180. Each computer 1300 operates under control of a central processor unit (CPU) 1302, such as a high-end microprocessor, e.g., typically found in Silicon Graphics workstation, and associated integrated circuit chips. A computer user can input commands and data from a keyboard and mouse 1312 and can view inputs and computer output at a display 1310. The display is typically a video monitor or flat panel display device. The computer 1300 also includes a direct access storage device (DASD) 1304, such as a fixed hard disk drive. The memory 1306 typically comprises volatile semiconductor random access memory (RAM). Each computer preferably includes a program product reader 1314 that accepts a program product storage device 1316, from which the program product reader can read data (and to which it can optionally write data). The program product reader can comprise, for example, a disk drive, and the program product storage device can comprise removable storage media such as a floppy disk, an optical CD-ROM disc, a CD-R disc, a CD-RW disc, DVD disk, or the like. In the preferred embodiment, each computer 1300 can communicate with the other connected computers over the network 1320 through a network interface 1308 that enables communication over a connection 1318 between the network and the computer. This facilitates having each separate system as illustrated in FIG. 1, provide inputs and outputs to the other components in the system.

The CPU 1302 operates under control of programming steps that are temporarily stored in the memory 1306 of the computer 1300. When the programming steps are executed, the pertinent system component performs its functions. Thus, the programming steps implement the functionality of the system components illustrated in the figures. The programming steps can be received from the DASD 1304, through the program product 1316, or through the network connection 1318. The storage drive 1304 can receive a program product, read programming steps recorded thereon, and transfer the programming steps into the memory 1306 for execution by the CPU 1302. As noted above, the program product storage device can comprise any one of multiple removable media having recorded computer-readable instructions, including magnetic floppy disks, CD-ROM, and DVD storage discs. Other suitable program product storage devices can include magnetic tape and semiconductor memory chips. In this way, the processing steps necessary for operation in accordance with the invention can be embodied on a program product.

Alternatively, the program steps can be received into the operating memory 1306 over the network 1318. In the network method, the computer receives data including program steps into the memory 1306 through the network interface 1308 after network communication has been established over the network connection 1318. The program steps are then executed by the CPU 1302 to implement the processing of the present invention.

Although the present invention is implemented on UNIX workstations, typical personal computers could likely be adopted to perform these functions in the future.

It should be understood that all of the computers of the systems embodying the various systems illustrated in FIG. 1, preferably have a construction similar to that shown in FIG. 13, so that details described with respect to the FIG. 13 computer 1300 will be understood to apply to all computers or components of the system. Any of the computers can have an alternative construction, so long as they have sufficient resources and processing power to handle finite element analyses and other functions in accordance with the present invention.

Those skilled in the art will recognize that variations in the steps, as well as the order of execution, may be done and still make the various embodiments of the invention operate. Furthermore, one skilled in the art will realize that although the examples described herein generally refer to TPEGs, other medical devices may be designed in accordance with the present invention.

In addition, although the modules of the system 105 (FIG. 1), the Geometry Generator, the Mesh Generator, Stress/Strain/Deformation Analyzer, and the Visualization module, are shown in different boxes, depending on the software tools utilized their functions may with each other. Some functions, for example, that are done by one module, e.g., the Mesh Generator, TRUEGRID, thus, may also be done by the Geometry Generator, MIMICS, or vice versa.

Embodiments of the present invention have been described above so that an understanding of the present invention can be conveyed. There are, however, many alternative software programs available or able to be written that would embody the functions of the present invention, and thus, may be used accordingly. The present invention should therefore not be seen as limited to the particular embodiments described herein, but rather, it should be understood that the present invention has wide applicability with respect to medical device design generally. All modifications, variations, or equivalent arrangements and implementations that are within the scope of the attached claims should therefore be considered within the scope of the invention.

What is claimed is:

1. A medical device made by a process, comprising:
performing a computer implemented process, including:
acquiring three-dimensional volumetric data of at least one anatomical feature of a vascular system,
generating a geometric model of said anatomical feature(s),
receiving data representing a geometric model of a candidate medical device design,
receiving said geometric model of said anatomical feature(s),
generating a finite element model representing both said geometric model of said anatomical feature(s) and said geometric model of said candidate medical device design with a mesh generator,
receiving material properties of said anatomical feature(s) and said candidate medical device design,
receiving load data imposed on said candidate medical device design and said anatomical feature(s), and
simulating an interaction between said anatomical feature(s) and said candidate medical device design over at least one dynamic expansion and contraction cycle of the anatomical feature(s) with a stress/strain/deformation analyzer to determine the predicted stresses, strains, and deformation of said candidate medical device design by said load data;
modifying the candidate medical device design as enabled by the simulation of the interaction between said anatomical feature(s) and said candidate medical device design over at least one dynamic expansion and contraction cycle of the anatomical feature(s); and
fabricating the medical device based on the modified candidate medical device design of the computer implemented process.

2. The medical device of claim 1 wherein the process of making said medical device comprises fabricating an endovascular prosthesis.

3. The medical device of claim 2 wherein the process of making said endovascular prosthesis comprises fabricating a stent graft.

4. The medical device of claim 2 wherein the process of making said endovascular prosthesis comprises fabricating a cardiovascular stent.

5. The medical device of claim 1 wherein said simulated stresses, strains, and deformations imposed on said candidate medical device design comprise dynamic or quasi-static stresses, strains, and deformations.

6. The medical device of claim 1 wherein the step of simulating stresses, strains, and deformations is performed to a point of failure of said candidate medical device design.

7. A medical device made by a process, comprising:
performing a computer implemented process, including:
acquiring three-dimensional volumetric data of at least one anatomical feature of a vascular system of a particular individual with a geometry generator,
generating a geometric model of said anatomical feature(s),
receiving a geometric model of a candidate medical device with a mesh generator,
receiving said geometric model of said anatomical feature(s) with a mesh generator,
generating a finite element model representing both said geometric model of said anatomical feature(s) and said geometric model of said candidate medical device,
receiving material properties of said anatomical feature(s) and said candidate medical device,
receiving load data imposed on said anatomical feature(s) and said candidate medical device, and
simulating an interaction between said anatomical feature(s) and said candidate medical device with a stress/strain/deformation analyzer that simulates an interaction between the anatomical feature(s) and said medical device over at least one dynamic expansion and contraction cycle of the anatomical feature(s) to determine the predicted dynamic or quasi-static stresses, strains, and deformations of said candidate medical device due to the interaction of the medical device with the anatomical feature;
modifying the candidate medical device design as enabled by the simulation of the interaction between said anatomical feature(s) and said candidate medical device design over at least one dynamic expansion and contraction cycle of the anatomical feature(s); and
fabricating the medical device based on the modified candidate medical device design of the computer implemented process.

8. The medical device of claim 7 wherein the process of making said medical device comprises fabricating an endovascular prosthesis.

9. The medical device of claim 8 wherein the process of making said endovascular prosthesis comprises fabricating a stent graft.

10. The medical device of claim 8 wherein the process of making said endovascular prosthesis comprises fabricating a cardiovascular stent.

11. The medical device of claim 7 wherein said simulated stresses, strains, and deformations imposed on said candidate medical device design comprise dynamic or quasi-static stresses, strains, and deformations.

12. The medical device of claim 7 wherein the step of simulating stresses, strains, and deformations is performed to a point of failure of said candidate medical device design.

13. The medical device of claim 7 wherein the process of making the medical device further comprises long term structural integrity testing of said candidate medical device design by recreating a plurality of dynamic expansion and contraction cycles of the vascular system.

14. The medical device of claim 13 wherein recreating the plurality of dynamic expansion and contraction cycles of the vascular system comprises recreating an amount of cycles that would meet or exceed the amount of cycles that would be expected in a lifetime of the particular individual.

15. A medical device made by a process, comprising:
performing a computer implemented process, including:
receiving data representing a geometric model of at least one in vitro anatomical feature of a vascular system and a geometric model of a candidate medical device design,
generating a finite element model representing both said geometric model of said in vitro anatomical feature(s) and said geometric model of said candidate medical device design with a mesh generator,
receiving material properties of said in vitro anatomical feature(s) and said candidate medical device design,
receiving load data imposed on said in vitro anatomical feature(s) and said candidate medical device design, and
simulating an interaction between said in vitro anatomical feature(s) and said candidate medical device with a stress/strain/deformation analyzer that simulates an interaction between the anatomical feature(s) and said medical device over at least one dynamic expansion and contraction cycle of the anatomical feature(s) to determine the predicted stresses, strains, and deformations of said candidate medical device design by said load data;
modifying the candidate medical device design as enabled by the simulation of the interaction between said anatomical feature(s) and said candidate medical device design over at least one dynamic expansion and contraction cycle of the anatomical feature(s); and
fabricating the medical device based on the modified candidate medical device design of the computer implemented process.

16. The medical device of claim 15 wherein the process of making said medical device comprises fabricating an endovascular prosthesis.

17. The medical device of claim 16 wherein the process of making said endovascular prosthesis comprises fabricating a stent graft.

18. The medical device of claim 16 wherein the process of making said endovascular prosthesis comprises fabricating a cardiovascular stent.

19. The medical device of claim 15 wherein determining said simulated stresses, strains, and deformations imposed on said candidate medical device design comprises determining dynamic or quasi-static stresses, strains, and deformations.

20. The medical device of claim 15 wherein the step of simulating stresses, strains, and deformations is performed to a point of failure of said candidate medical device design.

21. The medical device of claim 15 wherein the process of making the medical device further comprises long term structural integrity testing of said medical device by recreating a plurality of dynamic expansion and contraction cycles of the vascular system.

22. The medical device of claim 21 wherein recreating the plurality of dynamic expansion and contraction cycles of the vascular system comprises recreating an amount of cycles that would meet or exceed the amount of cycles that would be expected in a lifetime of the particular individual.

23. A medical device made by a process, comprising:
performing a computer implemented process, including:
acquiring three-dimensional volumetric data of at least one anatomical feature of a patient,
generating a geometric model of said anatomical feature(s),
receiving data representing a geometric model of a candidate medical device design,
receiving said geometric model of said anatomical feature(s),
generating a finite element model representing both said geometric model of said anatomical feature(s) and said geometric model of said candidate medical device design with a mesh generator,
receiving material properties of said anatomical feature(s) and said candidate medical device design,
receiving load data imposed on said candidate medical device design and said anatomical feature(s), and
simulating an interaction between said anatomical feature(s) and said candidate medical device design over at least one dynamic expansion and contraction cycle of the anatomical feature(s) with a stress/strain/deformation analyzer to determine the predicted stresses, strains, and deformation of said candidate medical device design by said load data;
modifying the candidate medical device design as enabled by the simulation of the interaction between said anatomical feature(s) and said candidate medical device design over at least one dynamic expansion and contraction cycle of the anatomical feature(s); and
fabricating the medical device based on the modified candidate medical device design of the computer implemented process.

24. The medical device of claim 23 wherein the process of making said medical device comprises fabricating an endovascular prosthesis.

25. The medical device of claim 24 wherein the process of making said endovascular prosthesis comprises fabricating a stent graft.

26. The medical device of claim 24 wherein the process of making said endovascular prosthesis comprises fabricating a cardiovascular stent.

27. The medical device of claim 23 wherein simulating said stresses, strains, and deformations imposed on said candidate medical device design comprises simulating dynamic or quasi-static stresses, strains, and deformations.

28. The medical device of claim 23 wherein the step of simulating stresses, strains, and deformations is performed to a point of failure of said candidate medical device design.

* * * * *